(12) United States Patent
Lordan

(10) Patent No.: US 10,480,034 B2
(45) Date of Patent: *Nov. 19, 2019

(54) CANCER BIOMARKER AND DIAGNOSTIC

(71) Applicant: Jeffrey Lordan, London (GB)

(72) Inventor: Jeffrey Lordan, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/166,626

(22) Filed: Oct. 22, 2018

(65) Prior Publication Data

US 2019/0093178 A1  Mar. 28, 2019

Related U.S. Application Data

(63) Continuation of application No. 14/917,752, filed as application No. PCT/GB2014/052812 on Sep. 17, 2014, now Pat. No. 10,138,523.

(30) Foreign Application Priority Data

Sep. 20, 2013 (GB) .................................. 1316783.8

(51) Int. Cl.
| | | |
|---|---|---|
| *G01N 33/574* | (2006.01) | |
| *G01N 33/53* | (2006.01) | |
| *C12Q 1/6886* | (2018.01) | |

(52) U.S. Cl.
CPC ..... *C12Q 1/6886* (2013.01); *G01N 33/57419* (2013.01); *G01N 33/57484* (2013.01); *C12Q 2600/112* (2013.01); *C12Q 2600/118* (2013.01); *C12Q 2600/136* (2013.01); *C12Q 2600/158* (2013.01); *G01N 2333/914* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 8,053,183 B2* | 11/2011 | Nakamura | ........... | C12Q 1/6886 435/287.1 |
| 2006/0019256 A1* | 1/2006 | Clarke | ................ | C12N 5/0695 435/6.14 |
| 2007/0059717 A1* | 3/2007 | Pascual | ................ | C12Q 1/6883 435/6.11 |

* cited by examiner

*Primary Examiner* — Changhwa J Cheu
(74) *Attorney, Agent, or Firm* — Adam Warwick Bell; Matthew Rupert Kaser

(57) ABSTRACT

The application discloses new biomarkers and methods useful in the diagnosis, prognosis and/or monitoring of, or as a therapeutic or research target for, solid tumour cancers, such as colorectal cancer, based on measuring the biomarkers; and related kits and devices.

16 Claims, 2 Drawing Sheets

CANCER BIOMARKER AND DIAGNOSTIC

Figure 1:
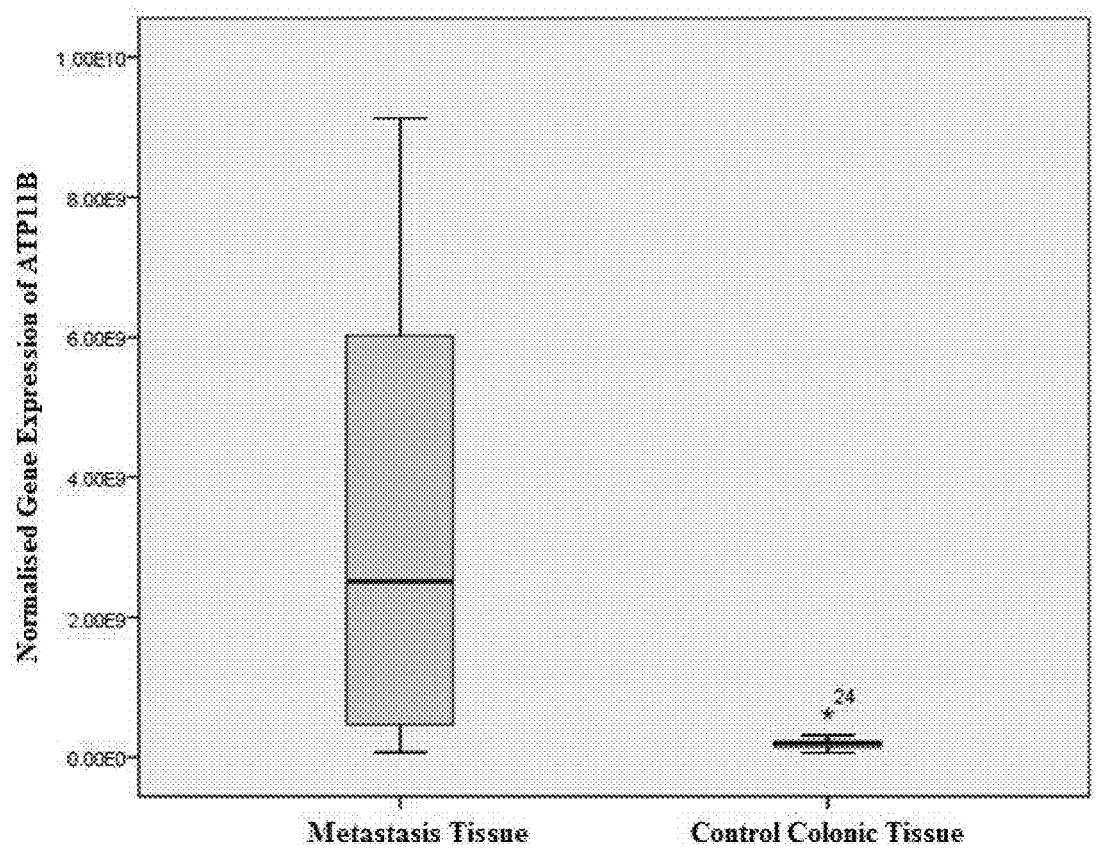

The present application is a continuation of Ser. No. 14/917,752 filed 9 Mar. 2016, which is incorporated by reference in its entirety for all purposes.

The invention relates to a biomarker, particularly to protein- and/or peptide-based biomarker, useful for the diagnosis, prognosis, monitoring and screening and/or as a target for the treatment of diseases and conditions in subjects, in particular solid tumour cancers such as colorectal cancer. The invention further concerns methods, uses, kits and devices involving or related to the biomarker.

Colorectal cancer, commonly known as colon cancer or bowel cancer, is a cancer from uncontrolled cell growth in the colon or rectum (parts of the large intestine), or in the appendix. Genetic analysis shows that essentially colon and rectal tumours are genetically the same cancer (Cancer Genome Atlas Network (19 Jul. 2012) *Nature* 487:330-337). Symptoms of colorectal cancer typically include rectal bleeding and anamia which are sometimes associated with weight loss and changes in bowel habit.

Most colorectal cancer occurs due to lifestyle and increasing age, with only a minority of cases associated with underlying genetic disorders. It typically starts in the lining of the bowel and if left untreated, can grow into the muscle layers of the bowel wall before breaching it, allowing metastatic spread. Cancers that are confined within the wall of the colon are often curable with surgery, while cancer that has spread widely around the body is usually not curable and management then focuses on extending the person's life via chemotherapy and improving quality of life. However, emerging studies have shown that metastatic spread to the liver, and/or lung can still potentially be cured with combinations of surgery and chemotherapy (Simmonds et al (2006) *British J. Cancer* 94:982-999; Wei et al (2006) *Annals of Surgical Oncology* 13:668-676; Nordlinger et al (2008) *Lancet* 371:1007-1016; Lordan & Karanjia (2008) *British J. Surgery* 95:128-129; Karanjia et al (2009) *Eur. J. Surg. Oncology* 35:65-70; Lordan et al (2009) *Eur. J. Surg. Oncology* 35:302-306; Karanjia et al (2009) *Eur. J. Surg. Oncology* 35:838-843; Lordan et al (2009) *Annals of the Royal College of Surgeons of England* 91:483-488; Lordan et al (2010) *Eur. J. Surg. Oncology* 36:47-51; Thomas et al (2011) *BJS* 10:1476-1482).

Colorectal cancer (CRC) is the second most common cause of cancer death in the Western world and more than 50% of patients develop metastatic spread. In the Western world in 2006, colorectal carcinoma (CRC) was the fourth most commonly diagnosed cancer and the second leading cause of cancer death. Indeed, recent reports have suggested rising occurrence (Simmonds et al (supra); McKay et al (2006) *British Journal of Surgery* 93:1192-1201). CRC was reported as the third most common cause of cancer death in the UK in 2006 (Cancer Research UK Information Resource Centre, 2006). Approximately 19,000 patients have died from colorectal cancer each year in the UK, with an incidence of 360 per 100,000 of the population (Gardner and Tweedle (2002) Pathology for Surgeons in Training. 3rd ed. Oxford University Press) and 40,000 new cases registered each year in the UK (NICE clinical guideline November 2011). In the USA, during 2011, there were 141,210 new cases of CRC and over 49,380 deaths attributed to the disease (American Cancer Society, 2012).

Currently, patients present to the General Practitioner (GP) with alarm symptoms. These include rectal bleeding, altered bowel habit, iron deficiency anemia, bowel obstruction, abdominal or rectal mass and unexplained weight loss. These symptoms trigger referral to a hospital specialist within two weeks, resulting in a clinic consultation.

During the clinic consultation, the specialist takes a more detailed history of the symptoms and examines the patient. At this point, special investigations are organised, including:
1. A colonoscopy to identify primary disease;
2. A computerised tomography (CT) scan of the thorax, abdomen and pelvis to look for metastatic spread; and
3. A blood test for the biomarker carcinoembryonic antigen (CEA), to look for evidence of the presence of colorectal cancer (either primary or metastatic).

The patient then returns to the clinic, typically four to six weeks later, to discuss the results of these tests with the specialist.

So far, the patient has spent an average of six to eight weeks from the point of presentation to the GP with worrying symptoms to the point of finally getting a diagnosis from the specialist with all the test results. This is a conservative estimation and, often, patients may spend several months in this pathway due to cancellations and miscommunication, worrying about their potential problem. In the UK at least, once the patient has a decision to treat, the clock starts and the hospital has 31 days to initiate that treatment.

Only 1-3% of these patients actually have a serious problem, i.e. colorectal cancer. This means that 97-99% of these patients need not have travelled through the pathway with all the associated worry and frustration. More crucially, for the 1-3% of patients who do actually have colorectal cancer, this time delay may mean the difference between having an operable, curable disease and having a terminal, untreatable disease.

In addition, the investigations organised by the specialist carry risk to each patient.

For colonoscopy, there is a risk of perforation in 1 in 1200 patients. Perforation is serious. At best, it may be treated with an abdominal drain (a tube inserted into the abdomen through the skin), antibiotics and many days in hospital under close observation. However, it often requires a major operation, typically with removal of part of the bowel, which may require a stoma (colostomy), followed by an indeterminate period of stay in the intensive care unit and the hospital in general (Hamilton and Sharp (2004) Family Practice 21:99-106).

Heavy bleeding can occur in 1 in 600 patients during or as a result of colonoscopy. This, as above, may be treated conservatively, but may also require intervention from the radiology department, or major surgery as above (Hamilton and Sharp supra).

Other complications from colonoscopy include post polypectomy syndrome, reaction to anaesthetic, infection, fluid and electrolyte disturbance, and severe dehydration due to the bowel preparation medication taken during the evening prior to colonoscopy.

Death from colonoscopy occurs in 1 in 14000 patients (Hamilton and Sharp supra) and the overall risk of complications during or resulting from colonoscopy is reported as 0.35%-3%.

The radiation exposure from a thorax, abdomen and pelvis staging CT scan is high, although it varies between patients and is most affected by body mass index (Israel et al (2010) *Am J Roentgenol.* 195:1342-1346). The most common complication from a CT scan is an allergic reaction to the contrast medium, which ranges from mild to potentially fatal (Israel et al supra). In addition, the intravenous contrast medium used for a CT scan can injure kidneys which may require admission to the intensive care unit for haemofiltration (kidney support; Israel et al supra).

Blood tests to determine the presence of CEA also carry risk. CEA has been shown to be elevated in 54% of patients with colorectal cancer, which is statistically slightly better than flipping a coin (Carpelan-Holmström et al (2002) *Anticancer Research* 22:2311-2316). However, obtaining the results of CEA can be a lengthy process. For hospital doctors in a large unit, the results may be available within 1-3 days after the blood is sent to the laboratory but, for a GP, the results may not be available for 2-3 weeks.

All the clinical tests that are currently carried out to detect colorectal cancer present a large financial obligation on the National Health Service (NHS) of the UK. For example, the cost of colonoscopy ranges from £1005-£2195 and, in the UK, approximately 750,000 to 1,500,000 colonoscopies are carried out per year (Bowles et al (2004) *Gut* 53:277-283). In addition, 14.2 million colonoscopies are carried out per year in the USA (Seeff et al (2004) *Gastroenterology* 127: 1670-1677).

The cost to the NHS of a CT scan varies from £500-£1500, while the cost of an individual CEA blood test is approximately £79.99. Indeed, the total cost of CEA blood tests to the NHS is approximately £80-160 million per year.

In the UK, there is currently a screening programme that has been designed to target people aged 60-69 who show no symptoms. The concept of screening is to detect cancer at an early stage, before the patient has symptoms. In theory, the earlier cancer is detected, the more likely the cancer is to be amenable to treatment.

In this screening programme, patients are sent a testing kit to provide a stool sample, that the laboratory uses to detect the presence of occult (or hidden) blood.

This test is called a faecal occult blood test (FOB). Patients who have blood detected in the stool are offered a screening colonoscopy.

However, even the screening programme has encountered problems. Firstly, due to its embarrassing nature, not all the patients targeted comply with the test. Secondly, accuracy is poor. This test is relatively sensitive, but not very specific. Therefore, there are a large number of false positives, which means a large proportion of patients who go on to have colonoscopy have no problems detected, which then introduces exposure to all the risks outlined above with colonoscopy.

Following treatment (chemotherapy alone, surgery alone, radiotherapy alone or combinations of these) for cancer, the doctors (either surgeons or oncologists, or both) follow up with the patient for a minimum of five years to check for evidence of disease recurrence.

For colorectal cancer, a typical surveillance regimen includes clinic appointments with the specialist at 3-6 weeks post treatment, then every three months during year 1 post-treatment, followed by every four months during year 2 post-treatment, every six months during years 3 post-treatment and once a year thereafter.

Patients typically have a CEA blood test at every clinic appointment. In addition, patients have two colonoscopies, one at year 1-2 and the second at year 4-5 following treatment. Patients also receive CT scans (particularly if they have been treated for metastatic disease) every six months for the first two years, and then yearly thereafter. The risks and costs of these tests have been described above.

Furthermore, due to the volume of patients, the gaps between consultations potentially allow cancers to recur between clinic and surveillance test appointments.

Thus, there is a clear need for a more reliable and cost effective method to detect colorectal cancers that presents lower risks to the patient and it is against this background that the present invention has been derived. In addition, a favourable outcome of therapeutic/surgical treatments is strongly correlated with early and/or accurate diagnosis, prognosis, monitoring, screening and/or target for treatment of a disease or condition. Therefore, there exists a continuous need for additional and preferably improved means for early and/or accurate diagnosis, prognosis, monitoring and/or screening as well as targets for treatment of diseases and conditions to guide and complement treatment choices.

In the present case, a biomarker has been identified that is closely indicative of solid tumour cancers, specifically colorectal cancer. In particular, the inventor has realised that up-regulation of the ATP11B gene and an increase in the quantity of ATP11B gene-derived protein in a biological sample derived from a subject or patient display a behaviour that is predictive and/or indicative of certain clinical outcomes that are highly relevant in the context of solid tumour cancers such as colorectal cancer.

Specifically, up-regulation of ATP11B gene expression and/or an increase in the resultant protein has been found by the inventor to be able to detect colorectal cancer with 100% accuracy respectively.

Probable phospholipid-transporting ATPase IF is an enzyme that, in humans, is encoded by the ATP11B gene (Nagase et al (1999) *DNA Res* 6(1):63-70; Halleck et al (2000) *Physiol Genomics* 1(3):139-50). P-type ATPases, such as ATP11B, are phosphorylated in their intermediate state and drive uphill transport of ions across membranes. Several subfamilies of P-type ATPases have been identified. One subfamily transports heavy metal ions, such as $Cu^{2+}$ or $Cd^{2+}$. Another subfamily transports non-heavy metal ions, such as $H^+$, $Na^+$, $K^+$, or $Ca^{2+}$. A third subfamily transports amphipaths, such as phosphatidylserine (www.ncbi.nlm.nih.gov/gene/23200).

Thus, in one aspect, the present invention provides the use of ATP11B gene up-regulation, and/or an increase in the quantity of protein or peptides resulting from ATP11B gene translation, as a biomarker, preferably as a biomarker for solid tumour cancers such as colorectal cancer. More preferably, ATP11B gene up-regulation and/or an increase the quantity of protein or peptides resulting from ATP11B gene translation, may be used as a biomarker for the diagnosis, prognosis, monitoring and/or screening of a solid tumour cancer in a subject.

The solid tumour cancer may be selected from the group consisting of: colorectal cancer; pancreatic cancer; primary liver cancers; kidney cancer; ovarian cancer; uterine cancer; lung cancer; breast cancer; prostate cancer; adipose tissue cancer; sarcoma, including gastrointestinal stromal tumours; skin cancer; small bowel cancer; stomach cancer; and oesophageal cancer.

In a particularly preferred embodiment, the solid tumour cancer may be colorectal cancer.

In one embodiment, the protein or peptides resulting from ATP11B gene translation is a P-type ATPase. The P-type ATPase may be Probable phospholipid-transporting ATPase IF.

In a preferred embodiment the present invention provides the use of ATP11B and S100A11 gene up-regulation, and/or an increase in the quantity of protein or peptides resulting from ATP11B and S100A11 gene translation, as a biomarker, preferably as a biomarker for solid tumour cancers such as colorectal cancer. More preferably, ATP11B and S100A11 gene up-regulation and/or an increase the quantity of proteins or peptides resulting from ATP11B and S100A11 gene translation, may be used as a biomarker for the diagnosis, prognosis, monitoring and/or screening of a solid tumour cancer in a subject.

The present uses may be adequately qualified as in vitro or ex vivo uses in that they apply particular in vitro or ex vivo processing and analysis on a biological sample obtained from a subject.

Currently, patients who present with alarm symptoms (see above) undergo a 6-8 week period of worry and concern while investigations are carried out. However, 97-99% of these patients have no cancer. In addition to the worry, the patients are exposed to the risk of the invasive investigations (see above).

The accuracy of the genes and gene products (proteins/peptides) of the present invention allows detection of the presence or absence of cancer with a greater accuracy. In turn, this means reassurance may be given to patients at the point of their first consultation with the GP and would not require further investigation and concern. These patients would not require exposure to the risk and inconvenience of the invasive investigations described above.

For the 1-3% of patients who turn out to have cancer, they will have waited 6-8 weeks before being given a diagnosis. The patient then requires a treatment plan, which involves a multi-disciplinary team meeting (which typically occurs once every week in a standard hospital). At this point, either a referral to the appropriate clinician is required, or a date for surgery needs to be made. Therefore, the actual treatment date is delayed further, in spite of the current UK Government stipulation that treatment must occur within 31 days from the decision to treat.

In contrast, the genes and gene products (proteins/peptides) of the present invention provide a quick and accurate detection of the presence of cancer at the point of first consultation with the GP. The two week referral to the specialist still needs to be instigated as these patients will require colonoscopy and CT scan to determine the site and extent of disease and to allow a treatment plan. However, more accurate detection at the first consultation will allow a GP to arrange the colonoscopy and CT scan during the time period in which the patient waits to see a specialist. This means that patients with cancer should see a specialist within two weeks and, at that point, a full and accurate diagnosis would be available to them, as well as the development of a treatment plan. In this way, patients with cancer should receive treatment much earlier than they currently experience. Indeed, it is expected that approximately four to six weeks of investigation time in the current system can be removed altogether.

Thus, a diagnostic test incorporating the detection of the genes and/or gene products of the present invention, it is likely to take two weeks from seeing the GP for a patient with suspected cancer to see a specialist and receive a treatment plan, followed by a stipulated maximum of 31 days to implement that treatment plan, according to current UK health guidelines.

The present invention also provides an opportunity for increased efficiency and cost saving within a national health system because 97-99% of patients presenting with alarm symptoms would not require CT, CEA blood test and colonoscopy due to the diagnostic accuracy of the genes and gene products identified herein. In monetary terms, it is estimated that the NHS in the UK would save approximately £500 million to £3 billion per year. Furthermore, a significant number of hospital clinic places would be available for patients who need them. Thus, the treatment process would become significantly more efficient for all concerned.

There are also predicted benefits to screening. As mentioned above, the UK carries out faecal occult blood testing on people between the ages of 60 and 69. The test requires the provision of a stool sample and has a low compliance rate due to the embarrassment of the test. In addition, the test is not accurate, providing a large number of false positives, thereby requiring a large number of people to undergo colonoscopy who turn out not to have cancer.

With the diagnostic of the present invention, it is expected that screening compliance and accuracy will be much greater. With a greater accuracy, only appropriate people will be referred for a surveillance colonoscopy, which would mean a wider age group of the population could potentially be targeted.

The diagnostic functionality and/or performance of the invention also provides speed, accuracy and cost saving benefits to post-treatment follow-up testing and monitoring in that a patient need only to visit his or her GP to assess the level of gene and/or protein/peptide expression. Patients would only need to see a specialist if the test shows a raised gene and/or protein expression level(s). This would free up clinic and investigation appointments for patients who need them. Also, patients would not be restricted to 4 monthly, 6 monthly or yearly appointments, but could be tested more frequently by a GP practice nurse, for example.

In another aspect, the present invention provides a method for the diagnosis, prognosis, monitoring and/or screening of a solid tumour cancer, such as colorectal cancer, in a subject, wherein the method comprises measuring ATP11B gene expression and/or the quantity of protein or peptides resulting from ATP11B gene translation, wherein either an increase in gene expression (i.e. gene up-regulation) or an increase in protein quantity above a constitutive or baseline level indicates that a solid tumour, or pre-cancer state, such as one or more polyps may be present, or a transcription of quantity level at a constitutive or baseline level indicates that no solid tumour is present.

Measurement of a change in ATP11B gene expression and/or translation, thereby allows the diagnosis of a solid tumour cancer or pre-cancer state /polyp.

In one embodiment, identification of ATP11B gene expression at a level above a constitutive or baseline level indicates gene up-regulation and may be used as a screen or primary diagnostic to identify that the subject may have or is at risk of developing colorectal cancer. On the basis of the finding, the patient may then be referred for further investigations to confirm the diagnosis, tumour location or prognosis.

In another embodiment, identification of ATP11B gene expression at a level of constitutive expression, or a decrease in transcription may be used to indicate that no tumour is present.

In an alternative embodiment, a measured level of ATP11B gene expression and/or gene-derived proteins or peptides above a constitutive or baseline level may be used as a screen or primary diagnostic or screen to identify that a subject may have or is at risk of developing colorectal cancer. Alternatively, a measured level of ATP11B gene expression and/or gene-derived protein or peptide that is substantially the same or similar to a constitutive level of expression may be used to indicate that no tumour is likely to be present.

In a preferred embodiment, the present invention provides a method for the diagnosis, prognosis, monitoring and/or screening of a solid tumour cancer, such as colorectal cancer, in a subject, wherein the method comprises measuring ATP11B and S100A11 gene expression and/or the quantity of proteins or peptides resulting from ATP11B and S100A11 gene translation, wherein either an increase in gene expression (i.e. gene up-regulation) or an increase in protein quantity above a constitutive or baseline level indicates that a solid tumour, or pre-cancer state, such as one or more polyps may be present, or a transcription of quantity level at a constitutive or baseline level indicates that no solid tumour is present.

It will be understood that methods for the diagnosis, prognosis, monitoring and/or screening of diseases and conditions generally comprise an examination phase in which data is collected from and/or about the subject.

Gene up-regulation is preferably measured, identified or quantified by an increase in gene transcription, an increase or the presence of RNA derived from the genes, transcription of the DNA, or an increase in markers, such as transcription factors, for transcription of the genes.

Suitable methods to measure, identify and/or quantify gene up-regulation are well known to the skilled person and include, for example, spectroscopic quantification, Q-PCR, QRT-PCR, DNA microarray, gel electrophoresis and next generation array sequencing.

Measurement, identification or quantification of protein or peptides derived from ATP11B and S100A11 gene translation may be effected by any suitable method. Such methods are well known to the skilled person and include microscopy and protein immunostaining, protein immunoprecipitation, immunoelectrophoresis, immunoblotting, Western blot, spectrophotometry, spectroscopy, immuno-labelling, antibody detection and enzyme assay such as ELISA.

In particularly preferred embodiments, the present biomarkers may be protein-, polypeptide-, peptide or nucleotide-based biomarkers. Particularly preferably, such biomarkers may be detected in blood, plasma or serum samples.

In a preferred embodiment, the present method for the diagnosis, diagnosis, prognosis, monitoring and/or screening of a solid tumour cancer in a subject may comprise:
(i) measuring ATP11B gene expression and/or the quantity of protein or peptides resulting from ATP11B gene translation in a biological sample from the subject, and
(ii) comparing the measurement and/or quantity measured in (i) with a reference value of the quantity of gene expression or proteins or peptides resulting from ATP11B gene translation, wherein the reference value represents a constitutive level of the gene expression and/or translation;
and wherein either a) gene expression or protein/peptide quantity above the reference value indicates that a solid tumour may be present, or b) a gene expression measurement or protein/peptide quantity substantially at or similar to the reference value indicates that no solid tumour is present.

In a particularly preferred embodiment, the present method for the diagnosis, diagnosis, prognosis, monitoring and/or screening of a solid tumour cancer in a subject may comprise:
(i) measuring ATP11B and S100A11 gene expression and/or the quantity of proteins or peptides resulting from ATP11B and S100A11 gene translation in a biological sample from the subject, and
(ii) comparing the measurement and/or quantity measured in (i) with a reference value of the quantity of gene expression or proteins or peptides resulting from ATP11B and S100A11 gene translation, wherein the reference value represents a constitutive level of the gene expression and/or translation;
and wherein either a) gene expression or protein/peptide quantity above the reference value indicates that a solid tumour may be present, or b) a gene expression measurement or protein/peptide quantity substantially at or similar to the reference value indicates that no solid tumour is present.

To assist with monitoring of subjects, it is particularly preferred if the reference value is obtained from the subject, as part of an on-going screening programme. Alternatively, the reference value may be obtained from a population of subjects who have no solid tumour cancer.

As set out above, the solid tumour cancer may be selected from the group consisting of: colorectal cancer; pancreatic cancer; primary liver cancers; kidney cancer; ovarian cancer; uterine cancer; lung cancer; breast cancer; prostate cancer; adipose tissue cancer; sarcoma, including gastrointestinal stromal tumours; skin cancer; small bowel cancer; stomach cancer; and oesophageal cancer. Preferably, the solid tumour cancer is colorectal cancer.

Related embodiments of the invention concern a method for making a diagnosis and/or prognosis of a solid tumour cancer, such as colorectal cancer, in a subject comprising:
(i) receiving data representative of values of the level of ATP11B gene expression and/or the quantity of proteins or peptides resulting from ATP11B gene translation in a sample from the subject;
(ii) accessing a data repository on a computer, said data repository comprising a reference value of the quantity or level of said one or more markers, said reference value representing a value for constitutive ATP11B gene and/or protein expression; and
(iii) comparing the data as received in (i) with the reference value in the data repository on the computer, thereby making a diagnosis and/or prognosis of a solid tumour cancer in the subject.

In a preferred embodiment, data representative of values of the levels of ATP11B and S100A11 gene expression and/or the quantity of proteins or peptides resulting from ATP11B and S100A11 gene translation are received.

In certain embodiments, the determination of what action is to be taken, e.g., by a clinician, in view of the diagnosis and/or prognosis is performed by a (the) computer. In certain embodiments, a (the) computer reports (i.e., generates an electronic report of) the action to be taken, preferably substantially in real time.

Throughout the present disclosure, methods and uses for the prognosis of solid tumour cancers may inter alia make a prognosis of the progression, aggravation, alleviation or recurrence of the disease or response to treatment.

In further preferred embodiments, the present method for monitoring a solid tumour cancer in a subject may comprise the steps of:
(i) measuring the quantity of ATP11B gene expression or the quantity of protein or peptides resulting from ATP11B gene translation in samples from the subject from two or more successive time points;
(ii) comparing the quantity of the one or more markers between the samples as measured in (i);
(iii) finding a deviation or no deviation of the quantity of the one or more markers between the samples as compared in (ii); and
(iv) attributing the finding of deviation or no deviation to a change in the solid tumour cancer in the subject between the two or more successive time points.

In an alternative embodiment, the quantity of ATP11B and S100A11 gene expression or the quantity of proteins or peptides resulting from ATP11B and
S100A11 gene translation is measured.

Such method thus allows the monitoring of the solid tumour cancer in a subject over time. In a preferred embodiment, the solid tumour cancer may be colorectal cancer.

Throughout the present disclosure, methods and uses for monitoring solid tumour cancers as taught herein may inter alia allow the monitoring of the progression, aggravation, alleviation or recurrence of the disease, or response to treatment. Advantageously, such monitoring methods may be applied in the course of a medical treatment of the subject, preferably medical treatment aimed at alleviating the cancer. Such monitoring may be included in decision making as to whether a patient may be discharged or needs a change in treatment.

In certain preferred embodiments, methods and uses for monitoring a solid tumour cancer, such as colorectal cancer, may be applied to monitor the effectiveness of cancer therapy or to decide on initiation, continuation or discontinuation (ending) of the therapy. Suitable therapies may include, for example, radiotherapy, chemotherapy, surgery or a combination of these therapies either sequentially or simultaneously.

In certain embodiments, the invention relates to a method for treating a solid tumour cancer, such as colorectal cancer, in a subject in need of said treatment, the method comprising:
(i) measuring the quantity of ATP11B gene expression and/or the quantity protein or peptides resulting from ATP11B gene translation in a biological sample from the subject, and
(ii) comparing the quantity measured in (i) with a reference value of the quantity of gene expression or proteins or peptides resulting from ATP11B gene translation, wherein the reference value represents a constitutive level of the gene expression and/or translation;
wherein either a) gene expression or protein/peptide quantity above the reference value indicates that a solid tumour may be present, or b) a gene transcription measurement or protein/peptide quantity substantially at or similar to the reference value indicates that no solid tumour is present, the method further comprising administering radiotherapy or chemotherapy or carrying out surgery, or a combination thereof if the presence of a solid tumour is indicated.

In an alternative embodiment, the quantity of ATP11B and S100A11 gene expression and/or the quantity of proteins or peptides resulting from ATP11B and S100A11 gene translation is measured.

The present invention also resides in the use of ATP11B genes and/or the protein or peptides resulting from ATP11B gene translation as therapeutic or biological research target for the treatment and/or investigation of solid tumour cancers such as colorectal cancer as herein described above.

An alternative embodiment encompasses the use of ATP11B and S100A11 genes and/or the proteins or peptides resulting from ATP11B and S100A11 gene translation as a therapeutic or biological research target.

Thus, the invention encompasses an assay for use in identifying agents that reduce expression and/or translation of ATP11B or that bind to the protein or peptides resulting from ATP11B gene translation. Specifically, an assay is provided to measure the inhibition of ATP11B gene expression and/or translation under varying conditions. The expression/translation altering or binding agents include small molecules, peptides, polynucleotides, antibodies, Fab fragments and aptamers.

The invention also encompasses an assay for use in identifying agents that reduce expression and/or translation of ATP11B and S100A11 or that bind to the protein or peptides resulting from ATP11B and S100A11 gene translation. Specifically, an assay is provided to measure the inhibition of ATP11B and S100A11 gene expression and/or translation under varying conditions.

In one embodiment, the agent is selected from the group consisting of: a monoclonal antibody, a polyclonal antibody, a peptide and a small molecule.

In another embodiment, the agent is selected from the group consisting of an organism molecule, a natural product a peptide, an oligosaccharide, a nucleic acid, a lipid, an antibody or binding fragment thereof, an aptamer and a cell.

In a yet further embodiment, the agent is from a library of compounds. As with all embodiments, the library may be selected from the group consisting of a random peptide library, a natural products library, a combinatorial library, an oligosaccharide library and a phage display library.

In any of the uses or methods as disclosed herein the measurement of ATP11B gene expression and/or translation may be advantageously combined with the assessment of one or more other biomarkers relevant for the diagnosis, prognosis, monitoring, screening and/or treatment of solid tumour cancers such as colorectal cancer.

References throughout this specification to "other (bio) markers" generally encompasses such other markers which are useful for the diagnosis, prediction, prognosis, monitoring and/or screening of solid tumour cancers such as colorectal cancer, as well as those biomarkers which provide targets for the treatment of such cancers.

A particularly preferred other biomarker is S100A11. S100 calcium binding protein A11 (S100A11) is a protein that is encoded by the S100A11 gene in humans (Wicki et al (1997) *Cell Calcium* 20(6):459-464). The protein encoded by this gene is a member of the S100 family of proteins containing two EF-hand calcium-binding motifs. S100 proteins are localised in the cytoplasm and/or nucleus of a wide range of cells and are believed to be involved in the regulation of a number of cellular processes such as cell cycle progression and differentiation. This protein may function in motility, invasion, and tubulin polymerisation. In addition, chromosomal rearrangements and altered expression of this gene have been implicated in tumour metastasis (www.ncbi.nlm.nih.gov/gene/6282).

Up-regulation of S100A11 gene expression and/or an increase in the resultant protein, S100 calcium binding protein A11 (also termed calgizzarin), has been found by the inventor to be able to detect colorectal cancer with 96.7% accuracy.

Additional other biomarkers include, for example, carcinoembryonic antigen (CEA), cancer antigen 19-9 (CA19-9), carcinoembryonic antigen-related cell adhesion molecule 1 (CEACAM1), cancer antigen 125 (CA125), alpha-fetoprotein (AFP), breast cancer type 1 susceptibility protein/breast cancer type 2 susceptibility protein (BRCA1/BRCA2), Human Epidermal Growth Factor Receptor 2 (HER-2), mast/stem cell growth factor receptor (SCFR), serine/threonine-protein kinase B-Raf (BRAF), anaplastic Lymphoma Kinase (ALK), Epidermal Growth Factor Receptor (EGFR), KRAS, UDP-glucuronosyltransferase 1-1 (UGT-A1), C-reactive protein, Human epididymis protein 4 (HE4), neuron-specific enolase (NSE), cytokeratin 19 (CYFRA-21-1), ferritin, prostate specific antigen (PSA), Death Receptor 6 protein (DR6), vascular endothelial growth factor (VEGF) and platelet-derived growth factor receptor A (PDGFRA).

Hence, the present uses and methods may further comprise measuring the presence or absence and/or quantity of one or more biomarkers selected from S100A11, carcinoembryonic antigen (CEA), cancer antigen 19-9 (CA19-9), carcinoembryonic antigen-related cell adhesion molecule 1 (CEACAM1), cancer antigen 125 (CA125), alpha-fetoprotein (AFP), breast cancer type 1 susceptibility protein/breast cancer type 2 susceptibility protein (BRCA1/BRCA2), Human Epidermal Growth Factor Receptor 2 (HER-2), mast/stem cell growth factor receptor (SCFR), serine/threonine-protein kinase B-Raf (BRAF), anaplastic Lymphoma Kinase (ALK), Epidermal Growth Factor Receptor (EGFR), KRAS, UDP-glucuronosyltransferase 1-1 (UGT-A1), C-reactive protein, Human epididymis protein 4 (HE4), neuron-specific enolase (NSE), cytokeratin 19 (CYFRA-21-1), ferritin, prostate specific antigen (PSA), Death Receptor 6 protein (DR6), vascular endothelial growth factor (VEGF) and platelet-derived growth factor receptor A (PDGFRA).

It will be appreciated that the presence or absence and/or quantity of such other biomarkers may be evaluated each separately and independently, or the presence or absence and/or quantity of such other biomarkers may be included in measurement of ATP11B gene expression and/or the quantity protein or peptides resulting from ATP11B gene translation.

Any one use or method as taught herein may preferably allow for sensitivity and/or specificity (preferably, sensitivity and specificity) of at least 50%, at least 60%, at least 70% or at least 80%, e.g., ≥85% or ≥90% or ≥95%, e.g., between about 80% and 100% or between about 85% and 95%.

Reference throughout this specification to "diseases", "conditions" or a similar reference encompasses any such diseases and conditions as disclosed herein insofar consistent with the context of a particular recitation. More specifically, such disease and conditions encompass solid tumour cancers, in particular colorectal cancer.

The uses and methods for the diagnosis, prognosis, monitoring and/or screening of a solid tumour cancer as taught herein may be used in subjects who have not yet been diagnosed as having such (for example, preventative screening), or who have been diagnosed as having such, or who are suspected of having such (for example, display one or more characteristic signs and/or symptoms). The uses and methods may also be used to detect response of the solid tumour cancer to therapeutic treatment or surgical intervention. The uses and methods may furthermore be used to help a medical practitioner decide upon worsening, status-quo, partial recovery, or complete recovery of the subject from the solid tumour cancer, resulting in either further treatment or observation or in discharge of the patient from medical care.

Reference values as employed herein may be established according to known procedures previously employed for other biomarkers. Such reference values may be established either within (i.e., constituting a step of) or external to (i.e., not constituting a step of) any one of the methods as taught herein. Accordingly, any one of the methods taught herein may comprise a step of establishing a reference value for the quantity of one or more markers as taught herein, said reference value representing a constitutive or baseline level of ATP11B gene expression and/or the quantity protein or peptides resulting from ATP11B gene translation.

The quantity of any one or more markers as taught herein and/or the presence or absence and/or quantity of the one or more other biomarkers (e.g., CEA), may be measured by any suitable technique such as may be known in the art.

For example, one may employ binding agents capable of specifically binding to the respective biomarkers and/or to fragments or parts thereof. Binding agent may be inter alia an antibody, aptamer, photoaptamer, protein, peptide, peptidomimetic or a small molecule. For instance, immunoassay technology or mass spectrometry analysis method or chromatography methods may be used, or RNA analysis tools such as northern blotting, or (quantitative) RT-PCR, or a combination of such methods.

Accordingly, further disclosed herein are the methods as taught herein, wherein the level of ATP11B gene expression and/or the quantity of protein or peptides resulting from ATP11B gene translation and/or the presence or absence and/or quantity of the one or more other biomarkers (e.g., CEA), is/are measured using a binding agent capable of specifically binding to the respective markers, an immunoassay technology, a mass spectrometry analysis method, a chromatography method, RNA analysis tools such as northern blotting, or (quantitative) RT-PCR, or a combination of such methods, preferably using an immunoassay technology, a mass spectrometry analysis method, a chromatography method, or a combination of the methods.

In preferred embodiments of the methods as taught herein, the quantity or level of ATP11B gene expression and/or the quantity protein or peptides resulting from ATP11B gene translation and/or the presence or absence and/or quantity of the one or more other biomarkers (e.g., CEA), is/are measured using an immunoassay technology, in preferred but non-limiting examples, using enzyme-linked immunosorbent assay (ELISA), radioimmunoassay (RIA), or ELISPOT technologies, preferably using ELISA.

In preferred embodiments of the methods as taught herein, the quantity or level of ATP11B gene expression and/or the quantity protein or peptides resulting from ATP11B gene translation and/or the presence or absence and/or quantity of the one or more other biomarkers (e.g., CEA), is/are measured using a binding agent capable of specifically binding to the respective markers, in preferred but non-limiting examples, using an aptamer, antibody, photoaptamer, protein, peptide, peptidomimetic, or a small molecule, preferably using an aptamer or antibody, more preferably using an aptamer.

Exemplary non-limiting specific antibodies for proteins or peptides resulting from ATP11b gene expression are commercially available, for instance, Catalogue No. HPA036237 from Sigma Aldrich.

Further disclosed is a kit, in particular for the diagnosis, prognosis and/or monitoring of a solid tumour cancer as taught herein in a subject, the kit comprising:
(i) means for measuring the quantity or level of ATP11B gene expression and/or the quantity protein or peptides resulting from ATP11B gene translation, in a sample from the subject; and optionally and preferably
(ii) a reference value of the quantity or level of ATP11B gene expression and/or the quantity protein or peptides resulting from ATP11B gene translation, wherein the reference value represents a baseline or constitutive level of expression in a subject having no solid tumour cancer.

In an alternative embodiment, the kit comprises means for measuring the quantity of level of ATP11B and S100A11 gene expression and/or the quantity protein or peptides resulting from ATP11B and S100A11 gene translation, in a sample from the subject; and optionally and preferably a reference value of the quantity or level of ATP11B and S100A11 gene expression and/or the quantity protein or peptides resulting from ATP11B and S100A11 gene translation, wherein the reference value represents a baseline or constitutive level of expression in a subject having no solid tumour cancer.

Thus, the kit allows:

measurement of the quantity or level of ATP11B (and optionally S100A11) gene expression and/or the quantity protein or peptides resulting from ATP11B (and optionally S100A11) gene translation in the sample from the subject by means (i);

comparison of the quantity of ATP11B (and optionally S100A11) gene expression and/or the quantity protein or peptides resulting from ATP11B (and optionally S100A11) gene translation measured by means (i) with the reference value of (ii);

finding a deviation or no deviation of the quantity or level of ATP11B (and optionally S100A11) gene expression and/or the quantity protein or peptides resulting from ATP11B (and optionally S100A11) gene translation measured by means (i) from the reference value of (ii); and consequent attribution of the finding of deviation or no deviation to a particular diagnosis and/or prognosis of a solid tumour cancer in the subject.

The means for measuring the quantity of ATP11B gene expression and/or the quantity protein or peptides resulting from ATP11B gene translation in the kits of the present invention may comprise, respectively, one or more binding agents capable of specifically identifying ATP11B gene expression and/or binding to a protein or peptides resulting from ATP11B gene translation. A binding agent may be inter alia an antibody, aptamer, photoaptamer, protein, peptide, peptidomimetic or a small molecule.

The means for measuring the quantity of ATP11B gene expression and/or the quantity protein or peptides resulting from ATP11B gene translation in the kits may also include means for measuring the quantity of S100A11 gene expression and/or the quantity protein or peptides resulting from S100A11.

Preferably, the present kits comprise one or more binding agents capable of specifically identifying ATP11B (and optionally S100A11) gene expression and/or binding to a protein or peptides resulting from ATP11B (and optionally S100A11) gene translation as taught herein, such as one or more aptamers, antibodies, photoaptamers, proteins, peptides, peptidomimetics or small molecules, preferably one or more aptamers or antibodies, more preferably one or more aptamers capable of specifically binding to said one or more markers as taught herein. A binding agent may be advantageously immobilised on a solid phase or support.

The present kits may employ an immunoassay technology or mass spectrometry analysis technology or chromatography technology, or a combination of such technologies. Preferably the present kits employ an immunoassay technology, in preferred but non-limiting examples, enzyme-linked immunosorbent assay (ELISA), radioimmunoassay (RIA), or ELISPOT technologies, preferably using ELISA. Hence, the means for measuring the quantity or level of marker(s) may be an immunoassay, e.g., an immunoassay employing antibody(ies) and/or aptamers, e.g., ELISA, RIA, or ELISPOT assay.

Therefore, also disclosed is a kit, particularly a kit for the diagnosis, prognosis and/or monitoring of a solid tumour cancer as taught herein comprising:

(i) one or more binding agents capable of specifically identifying ATP11B gene expression or binding ATP11B gene-derived protein and/or peptides;

(ii) preferably, a known quantity, level or concentration of ATP11B gene expression and/or ATP11B gene-derived protein and/or peptides (e.g., for use as controls, standards and/or calibrators);

(iii) preferably, a reference value of the quantity or level of ATP11B gene expression and/or ATP11B gene-derived proteins and/or peptides.

The one or more binding agents may also be capable of or include agents capable of indentifying S100A11 gene expression and/or S100A11 gene-derived proteins and/or peptides. Alternatively or in addition, the kit may comprise a known quantity, level or concentration of S100A11 expression and/or S100A11 gene-derived protein and/ore peptides.

The components under (i) and/or (iii) may be suitably labelled as taught elsewhere in this specification.

Further disclosed is the use of any one kit as described herein for the diagnosis, prognosis and/or monitoring of a solid tumour cancer, such as colorectal cancer, in a subject. In particular, disclosed is the use of any one kit as described herein comprising means for measuring the quantity or level of ATP11B (and optionally S100A11) gene expression and/or the quantity of protein or peptides resulting from ATP11B (and optionally S100A11) gene translation identified in this specification, in a sample from a subject, for performing any one of the methods as taught herein. Also intended herein is the use of any one kit as described herein, wherein the kit further comprises a reference value of the quantity or level of ATP11B (and optionally S100A11) gene expression and/or the quantity protein or peptides resulting from ATP11B (and optionally S100A11) gene translation or means for establishing said reference value, wherein the reference value represents a constitutive or baseline level of marker gene expression or protein/peptide quantity, either in a population or in the subject when no solid tumour is present.

Also disclosed are reagents and tools useful for measuring ATP11B gene expression and ATP11B gene-derived protein and/or peptides and optionally one or more other biomarkers such as those described hereinabove, particularly S100A11.

Hence, disclosed is a protein, polypeptide or peptide array or microarray comprising:

(a) ATP11B gene-derived proteins and/or peptides, preferably a known quantity or concentration of ATP11B gene-derived proteins and/or peptides; and (b) optionally and preferably, one or more other biomarkers such as S100A11, preferably a known quantity or concentration of the one or more other biomarkers useful for the diagnosis, prognosis, monitoring, and/or screening of a solid tumour cancer, such as colorectal cancer, as taught herein in a subject.

Further provided is the use of any one protein, polypeptide or peptide array or microarray as described herein, for the diagnosis, prognosis, monitoring and/or screening of a solid tumour cancer, or as a therapeutic target for the identification of suitable therapeutic or research treatment(s) as taught herein in a subject.

Further disclosed is the use of any one protein, polypeptide or peptide array or microarray as described herein for the diagnosis, prognosis, monitoring and/or screening of or as a therapeutic or research target for a solid tumour cancer in a subject. In a preferred embodiment, the solid tumour cancer is selected from the group consisting of: colorectal cancer; pancreatic cancer; primary liver cancers; kidney cancer; ovarian cancer; uterine cancer; lung cancer; breast cancer; prostate cancer; adipose tissue cancer; sarcoma, including gastrointestinal stromal tumours; skin cancer; small bowel cancer; stomach cancer; and oesophageal cancer.

Also disclosed is a binding agent array or microarray comprising:

(a) one or more binding agents capable of specifically binding to ATP11B gene-derived proteins and/or peptides, preferably a known quantity or concentration of such binding agents; and optionally and preferably (b) one or more binding agents useful for the diagnosis, prognosis, monitoring and/or screening or treatment of a solid tumour cancer as taught herein in a subject, preferably a known quantity or concentration of the binding agents.

The one or more binding agents may also be capable or may include agents capable of specifically binding to S100A11 gene-derived proteins and/or peptides.

Such binding agents may be as detailed elsewhere in this specification.

Further provided is the use of any one binding agent array or microarray as described herein, for the diagnosis, prognosis, monitoring and/or screening or as a target for the treatment of a solid tumour cancer as taught herein in a subject. In particular, disclosed is the use of any one binding agent array or microarray as described herein comprising one or more binding agents capable of specifically binding to ATP11B (and optionally S100A11) gene-derived protein and/or peptides, in a sample from a subject, for performing any one of the methods as taught herein. Also intended herein is the use of any one binding agent array or microarray as described herein, wherein the binding agent array or microarray further comprises one or more binding agents useful for the diagnosis, prognosis, monitoring and/or screening or as a target for the treatment of a solid tumour cancer as taught herein in a subject, preferably a known quantity or concentration of the binding agents.

Further disclosed is the use of any one binding agent array or microarray as described herein for the diagnosis, prognosis, monitoring and/or screening or as a target for the treatment of a solid tumour cancer, such as colorectal cancer.

Also disclosed are kits as taught here above configured as portable devices, such as, for example, bed-side devices.

A related aspect thus provides a portable testing device capable of measuring the quantity of ATP11B (and optionally S100A11) gene-derived proteins and/or peptides, in a sample from a subject comprising:

(i) means for obtaining a sample from the subject,
(ii) means for measuring the quantity or concentration of ATP11B (and optionally S100A11) gene-derived proteins and/or peptides, in the sample, and
(iii) means for visualising the quantity or concentration of ATP11B (and optionally S100A11) gene-derived proteins and/or peptides measured in the sample.

In an embodiment, the means of parts (ii) and (iii) may be the same, thereby providing a portable testing device capable of measuring the quantity or concentration of ATP11B (and optionally S100A11) gene-derived proteins and/or peptides in a sample from a subject comprising:

(i) means for obtaining a sample from the subject; and
(ii) means for measuring the quantity or concentration of ATP11B (and optionally S100A11) gene-derived proteins and/or peptides in the sample and visualising the quantity of ATP11B (and optionally S100A11) gene-derived proteins and/or peptides measured in the sample.

In a particular embodiment, the visualising means is capable of indicating whether the quantity or concentration of ATP11B (and optionally S100A11) gene-derived proteins and/or peptides in the sample is above or below a certain threshold level and/or whether the quantity or concentration of ATP11B (and optionally S100A11) gene-derived proteins and/or peptides in the sample deviates or not from a reference value of the quantity of ATP11B (and optionally S100A11) gene-derived proteins and/or peptides, the reference value representing a constitutive or baseline level of protein/peptide expression, either in a population or in a subject. Hence, the portable testing device may suitably also comprise the reference value.

Other aspects of the present invention relate to the realisation that up-regulation of ATP11B (and optionally S100A11) gene expression and an increase in the quantity of ATP11B (and optionally S100A11) gene-derived proteins and/or peptides may be valuable targets for therapeutic and/or prophylactic interventions in a solid tumour cancer as taught herein, particularly in colorectal cancer.

Hence, also disclosed herein are any one and all of the following:

(1) an agent that is able to modulate the level and/or the activity of any one or more of the ATP11B (and optionally S100A11) nucleic acids or proteins/peptides identified herein.

(2) use of an agent that is able to modulate the level and/or the activity of the one or more ATP11B (and optionally S100A11) nucleic acids or proteins/peptides as defined in (1) above for the manufacture of a medicament for the treatment of a solid tumour cancer, such as colorectal cancer, as taught herein; or use of an agent that is able to modulate the level and/or the activity of the one or more ATP11B (and optionally S100A11) nucleic acids or proteins/peptides as defined in (1) above for the treatment of a solid tumour cancer, such as colorectal cancer, as taught herein.

(3) a method for treating a solid tumour cancer, such as colorectal cancer, as taught herein in a subject in need of such treatment, comprising administering to said subject a therapeutically or prophylactically effective amount of an agent that is able to modulate the level and/or the activity of the one or more ATP11B (and optionally S100A11) nucleic acids or proteins/peptides as defined in (1) above.

(4) The subject matter as set forth in any one of (1) to (3) above, wherein the agent is able to reduce the level and/or the activity of the one or more ATP11B (and optionally S100A11) nucleic acids or proteins/peptides as defined in (1) above.

(5) The subject matter as set forth in any one of (1) to (4) above, wherein the agent is able specifically to bind to the one or more ATP11B (and optionally S100A11) nucleic acids or proteins/peptides as defined in (1) above.

(6) The subject matter as set forth in any one of (1) to (5) above, wherein the agent is an antibody or a fragment or derivative thereof; a polypeptide; a peptide; a peptidomimetic; an aptamer; a photoaptamer; or a chemical substance, preferably an organic molecule, more preferably a small organic molecule.

(7) The subject matter as set forth in any one of (1) to (4) above, wherein the agent is able to reduce or inhibit the expression of the one or more ATP11B (and optionally S100A11) nucleic acids or proteins/peptides as defined in (1) above, preferably wherein the agent is an antisense agent; a ribozyme; or an agent capable of causing RNA interference.

(8) The subject matter as set forth in any one of (1) to (4) above, wherein the agent is able to reduce or inhibit the level and/or activity of the one or more ATP11B (and optionally S100A11) nucleic acids or proteins/peptides as defined in (1) above, preferably wherein the agent is a recombinant or isolated deletion construct of the one or more ATP11B (and optionally S100A11) proteins/peptides as defined in (1) above, more preferably wherein the polypeptide has a dominant negative activity over the native one or more ATP11B (and optionally S100A11) proteins/peptides as defined in (1) above.

(9) An assay to select, from a group of test agents, a candidate agent potentially useful in the treatment of a solid tumour cancer as taught herein, the assay comprising determining whether a tested agent can reduce the level and/or activity of the one or more ATP11B (and optionally S100A11) nucleic acids or proteins/peptides as defined in (1) above.

(10) The assay as set forth in (9) above, further comprising use of the selected candidate agent for the preparation of a composition for administration to and monitoring of the prophylactic and/or therapeutic effect thereof in a non-human animal model, preferably a non-human mammal model, of a solid tumour cancer as taught herein.

(11) The agent isolated by the assay as set forth in (10) above.

(12) A pharmaceutical composition or formulation comprising a prophylactically and/or therapeutically effective amount of one or more agents as set forth in any one of (1) to (8) or (10) above, or a pharmaceutically acceptable N-oxide form, addition salt, prodrug or solvate thereof, and further comprising one or more of pharmaceutically acceptable carriers.

(13) A method for producing the pharmaceutical composition or formulation as set forth in (12) above, comprising admixing the one or more agents with the one or more pharmaceutically acceptable carriers.

The solid tumour cancer set forth in any one of (1) to (13) above is selected from the group consisting of: colorectal cancer; pancreatic cancer; primary liver cancers; kidney cancer; ovarian cancer; uterine cancer; lung cancer; breast cancer; prostate cancer; adipose tissue cancer; sarcoma, including gastrointestinal stromal tumours; skin cancer; small bowel cancer; stomach cancer; and oesophageal cancer. A particularly preferred cancer is colorectal cancer.

Also contemplated is thus a method (a screening assay) for selecting an agent capable of specifically binding to one or more ATP11B nucleic acids (and optionally S100A11) or proteins/peptides identified herein comprising: (a) providing one or more, preferably a plurality of, test binding agents; (b) selecting from the test binding agents of (a) those which bind to the one or more ATP11B (and optionally Si 00A11) nucleic acids or proteins/peptides; and (c) counter-selecting (i.e., removing) from the test binding agents selected in (b) those which bind to any one or more other, unintended or undesired, targets.

Binding between test binding agents and the one or more ATP11B (and optionally S100A11) nucleic acids or proteins/peptides may be advantageously tested by contacting (i.e., combining, exposing or incubating) the one or more ATP11B (and optionally S100A11) nucleic acids or proteins/peptides with the test binding agents under conditions generally conducive for such binding. For example and without limitation, binding between test binding agents and the one or more ATP11B (and optionally S100A11) nucleic acids or proteins/peptides may be suitably tested in vitro; or may be tested in host cells or host organisms comprising the one or more ATP11B (and optionally S100A11) nucleic acids or proteins/peptides and exposed to or configured to express the test binding agents.

Without limitation, the binding or modulating agents may be capable of binding the one or more ATP11B (and optionally S100A11) nucleic acids or proteins/peptides or modulating the activity and/or level of the one or more ATP11B (and optionally S100A11) nucleic acids or proteins/peptides in vitro, in a cell, in an organ and/or in an organism.

In the screening assays as set forth in any one of (9) and (10) above, modulation of the activity and/or level of the one or more ATP11B (and optionally S100A11) nucleic acids or proteins/peptides by test modulating agents may be advantageously tested by contacting (i.e., combining, exposing or incubating) the one or more ATP11B (and optionally S100A11) nucleic acids or proteins/peptides with the test modulating agents under conditions generally conducive for such modulation. By means of example and not limitation, where modulation of the activity and/or level of the one or more ATP11B (and optionally S100A11) nucleic acids or proteins/peptides results from binding of the test modulating agents to the one or more ATP11B (and optionally S100A11) nucleic acids or proteins/peptides, the conditions may be generally conducive for such binding. For example and without limitation, modulation of the activity and/or level of the one or more ATP11B (and optionally S100A11) nucleic acids or proteins/peptides by test modulating agents may be suitably tested in vitro; or may be tested in host cells or host organisms comprising the one or more ATP11B (and optionally S100A11) nucleic acids or proteins/peptides and exposed to or configured to express the test modulating agents.

The above and further aspects and preferred embodiments of the invention are described in the following sections and in the appended claims. The subject matter of appended claims is hereby specifically incorporated in this specification.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The term also encompasses "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of the members, or to any two or more of the members, such as, e.g., any ≥3, ≥4, ≥5, ≥6 or ≥7 etc. of the members, and up to all the members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

As noted, the inventor has identified increased ATP11B gene and/or protein expression as valuable biomarkers for identifying solid tumour cancers, such as colorectal cancer, in subjects.

The term "biomarker" is widespread in the art and may broadly denote a biological molecule and/or a detectable portion thereof whose qualitative and/or quantitative evaluation in a subject is predictive or informative (e.g., diagnostic and/or prognostic) with respect to one or more aspects of the subject's phenotype and/or genotype, such as, for example, with respect to the status of the subject as to a given disease or condition. Preferably, biomarkers as intended herein are peptide-, polypeptide- and/or protein-based. The terms "biomarker" and "marker" may be used interchangeably herein.

The terms "diagnosing" or "diagnosis", "prognosticating" or "prognosis" and "screening" are commonplace and well-understood in medical and clinical practice. It shall be understood that the phrase "a method for the diagnosis, prediction, prognosis and/or screening" of a given disease or condition may also be interchanged with phrases such as "a method for diagnosing, predicting, prognosticating and/or screening" the disease or condition or "a method for making (or determining or establishing) the diagnosis, prediction, prognosis and/or screening" of the disease or condition, or the like.

The terms "diagnosing" or "diagnosis" generally refer to the process or act of discovering, recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition). As used herein, "diagnosis of" the diseases or conditions as taught herein in a subject may particularly mean that the subject has such, hence, is diagnosed as having such. "Diagnosis of no" diseases or conditions as taught herein in a subject may particularly mean that the subject does not have such, hence, is diagnosed as not having such. A subject may be diagnosed as not having such despite displaying one or more conventional symptoms or signs reminiscent of such.

The terms "prognosticating" or "prognosis" generally refer to an anticipation on the progression of a disease or condition and the prospect (e.g., the probability, duration, and/or extent) of recovery. A good prognosis of the solid tumour cancers taught herein may generally encompass anticipation of a satisfactory partial or complete recovery from the cancer. A good prognosis of such may more commonly encompass anticipation of not further worsening or aggravating of such. A poor prognosis of a solid tumour cancer as taught herein may generally encompass anticipation of a substandard recovery and/or unsatisfactorily slow recovery, or to substantially no recovery or even further worsening of such.

Hence, prognosis of a disease or condition may inter alia allow the prognosis of the occurrence of a solid tumour cancer, or the prognosis of the progression, aggravation, alleviation or recurrence of a solid tumour cancer or response to treatment.

Further, monitoring a solid tumour cancer may inter alia allow the monitoring of the progression, aggravation, alleviation or recurrence of a solid tumour cancer, or response to treatment. Advantageously, monitoring may be applied in the course of medical treatment of a subject, preferably medical treatment aimed at alleviating the solid tumour cancer. Such monitoring may be comprised, e.g., in decision making whether a patient may be discharged, needs a change in treatment or needs further hospitalisation. As intended herein, a reference to monitoring of a solid tumour cancer also specifically includes monitoring of the probability, risk or chance of a subject developing a solid tumour cancer, i.e., monitoring change(s) in the probability, risk or chance over time.

The term "screening" refers to the targeting of a population, for example according to age, gender or some other parameter, who have no symptoms and actively looking for cancer or a pre-cancer state (polyp(s) etc) to obtain the best possible prognosis and detect the cancer early thereby increasing the chances of successful treatment.

The term "subject" or "patient" as used herein typically denotes humans, but may also encompass reference to non-human animals, preferably warm-blooded animals, even more preferably mammals, such as, e.g., non-human primates, rodents, canines, felines, equines, ovines, porcines, and the like. Subjects typically include both male and female genders.

The terms "sample" or "biological sample" as used herein include any biological specimen obtained from a subject. Samples may include, without limitation, whole blood, plasma, serum, red blood cells, white blood cells (e.g., peripheral blood mononuclear cells), saliva, urine, stool (i.e., faeces), tears, sweat, sebum, nipple aspirate, ductal lavage, tumour exudates, synovial fluid, cerebrospinal fluid, lymph, fine needle aspirate, amniotic fluid, any other bodily fluid, cell lysates, cellular secretion products, inflammation fluid, semen and vaginal secretions. Preferred samples may include ones comprising ATP11B gene-derived protein/peptides as taught herein in detectable quantities. In preferred embodiments, the sample may be whole blood or a fractional component thereof such as, e.g., plasma, serum, or a cell pellet. Preferably the sample is readily obtainable by minimally invasive methods, allowing the removal or isolation of the sample from the subject. Samples may also include tissue samples and biopsies, tissue homogenates and the like, such as skin, saliva, mouth mucosa, fat, and tumour biopsy.

Preferably, the sample used to detect the levels of ATP11B (and optionally S100A11) gene up-regulation or quantity of ATP11B (and optionally S100A11) gene-derived protein/peptides as taught herein is blood plasma. The term "plasma" generally denotes the substantially colourless watery fluid of the blood that contains no cells, but in which the blood cells (erythrocytes, leukocytes, thrombocytes, etc.) are normally suspended, containing nutrients, sugars, proteins, minerals, enzymes, etc.

Equally preferred, the sample used to detect the levels of ATP11B (and optionally S100A11) gene up-regulation or quantity of ATP11B (and optionally S100A11) gene-derived proteins/peptides as taught herein is serum. The term "serum" refers to the component of blood that is neither a blood cell nor a clotting factor; the term refers to the blood plasma with the fibrinogens removed.

A molecule or analyte such as a protein, polypeptide or peptide, or a group of two or more molecules or analytes such as two or more proteins, polypeptides or peptides, is "measured" in a sample when the presence or absence and/or quantity of the molecule or analyte or of the group of molecules or analytes is detected or determined in the sample, preferably substantially to the exclusion of other molecules and analytes.

The terms "quantity", "amount" and "level" are synonymous and generally well-understood in the art. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a constitutive or base-line level of the biomarker. These values or ranges may be obtained from an individual or from a population in which no solid tumour cancer is found.

An absolute quantity of a molecule or analyte in a sample may be advantageously expressed as weight or as molar amount, or more commonly as a concentration, e.g., weight per volume or mol per volume.

A relative quantity of a molecule or analyte in a sample may be advantageously expressed as an increase or decrease or as a fold-increase or fold-decrease relative to another value, such as relative to a reference value as taught herein. Performing a relative comparison between first and second parameters (e.g., first and second quantities) may but need not require determining first the absolute values of the first and second parameters. For example, a measurement method may produce quantifiable readouts (such as, e.g., signal intensities) for the first and second parameters, wherein the readouts are a function of the value of the parameters, and wherein the readouts may be directly compared to produce a relative value for the first parameter vs. the second parameter, without the actual need to first convert the readouts to absolute values of the respective parameters.

As used herein, the reference to any one marker (biomarker), nucleic acid, peptide, polypeptide or protein corresponds to the marker, nucleic acid, peptide, polypeptide or protein commonly known under the respective designations in the art. The terms encompass such markers, nucleic acids, proteins and polypeptides of any organism where found, and particularly of animals, preferably warm-blooded animals, more preferably vertebrates, yet more preferably mammals, including humans and non-human mammals, still more preferably of humans. The terms particularly encompass such markers, nucleic acids, proteins and polypeptides with a native sequence, i.e., ones of which the primary sequence is the same as that of the markers, nucleic acids, proteins and polypeptides found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to post-transcriptional or post-translational modifications. Any such variants or isoforms of markers, nucleic acids, proteins and polypeptides are intended herein. Accordingly, all sequences of markers, nucleic acids, proteins and polypeptides found in or derived from nature are considered "native". The terms encompass the markers, nucleic acids, proteins and polypeptides when forming a part of a living organism, organ, tissue or cell, when forming a part of a biological sample, as well as when at least partly isolated from such sources. The terms also encompass proteins and polypeptides when produced by recombinant or synthetic means.

The reference herein to any biomarker, nucleic acid, protein or polypeptide may also encompass fragments thereof. Hence, the reference herein to measuring (or measuring the quantity of) any one biomarker, nucleic acid, protein or polypeptide may encompass measuring the biomarker, nucleic acid, protein or polypeptide, such as, e.g., measuring the mature and/or the processed soluble/secreted form (e.g. plasma circulating form) thereof and/or measuring one or more fragments thereof.

For example, any biomarker, nucleic acid, protein or polypeptide and/or fragments thereof may be measured collectively, such that the measured quantity corresponds to the sum amounts of the collectively measured species. In another example, any biomarker, nucleic acid, protein or polypeptide and/or one or more fragments thereof may be measured each individually. Preferably, the fragment may be a plasma circulating (i.e., not cell- or membrane-bound) form. Without being bound by any theory, such circulating forms may be derived from full-length biomarkers, nucleic acids, proteins or polypeptides through natural processing, or may be resulting from known degradation processes occurring in a sample. In certain situations, the circulating form may also be the full-length biomarker, nucleic acid, protein or polypeptide, which is found to be circulating in the plasma. The "circulating form" may thus be any biomarker, nucleic acid, protein or polypeptide or any processed soluble form thereof or fragments of either one, that is circulating in the sample, i.e. which is not bound to a cell- or membrane fraction of the sample.

Unless otherwise apparent from the context, reference herein to any biomarker, nucleic acid, protein or polypeptide and fragments thereof may generally also encompass modified forms of the biomarker, nucleic acid, protein or polypeptide and fragments such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

In an embodiment, any biomarker, nucleic acid, protein or polypeptide and fragments thereof may be human, i.e., their primary sequence may be the same as a corresponding primary sequence of or present in a naturally occurring human biomarker, nucleic acid, protein or polypeptide. Hence, the qualifier "human" in this connection relates to the primary sequence of the respective biomarker, nucleic acid, protein or polypeptide, rather than to its origin or source. For example, such biomarker, nucleic acid, protein or polypeptide and fragments may be present in or isolated from samples of human subjects or may be obtained by other means (e.g., by recombinant expression, cell-free translation or non-biological peptide synthesis).

The term "isolated" with reference to a particular component (such as for instance, nucleic acid, protein, polypeptide, peptide or fragment thereof) generally denotes that such component exists in separation from—for example, has been separated from or prepared in separation from—one or more other components of its natural environment. For instance, an isolated human or animal nucleic acid, protein, polypeptide, peptide or fragment exists in separation from a human or animal body where it occurs naturally.

The term "isolated" as used herein may preferably also encompass the qualifier "purified". As used herein, the term "purified" with reference to nucleic acid(s), protein(s), polypeptide(s), peptide(s) and/or fragment(s) thereof does not require absolute purity. Instead, it denotes that such nucleic acid(s), protein(s), polypeptide(s), peptide(s) and/or fragment(s) is (are) in a discrete environment in which their abundance (conveniently expressed in terms of mass or weight or concentration) relative to other proteins is greater than in a biological sample. A discrete environment denotes a single medium, such as for example a single solution, gel, precipitate, lyophilisate, etc. Purified nucleic acids, peptides, polypeptides or fragments may be obtained by known methods including, for example, laboratory or recombinant synthesis, chromatography, preparative electrophoresis, centrifugation, precipitation, affinity purification, etc.

Purified protein(s), polypeptide(s), peptide(s) and/or fragment(s) may preferably constitute by weight ≥10%, more preferably ≥50%, such as ≥60%, yet more preferably ≥70%, such as ≥80%, and still more preferably ≥90%, such as ≥95%, ≥96%, ≥97%, ≥98%, 99% or even 100%, of the protein content of the discrete environment. Protein content may be determined, e.g., by the Lowry method (Lowry et al (1951) *J. Biol. Chem.* 193:265), optionally as described by Hartree 1972 (*Anal. Biochem.* 48:422-427). Also, purity of peptides or polypeptides may be determined by SDS-PAGE under reducing or non-reducing conditions using Coomassie blue or, preferably, silver stain.

In some embodiments, reagents disclosed herein may comprise a detectable label. The term "label" refers to any atom, molecule, moiety or biomolecule that may be used to provide a detectable and preferably quantifiable read-out or property, and that may be attached to or made part of an entity of interest, such as a peptide or polypeptide or a specific-binding agent. Labels may be suitably detectable by mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$, electron-dense reagents; enzymes (e.g. horse-radish phosphatise or alkaline phosphatise as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

For example, the label may be a mass-altering label. Preferably, a mass-altering label may involve the presence of a distinct stable isotope in one or more amino acids of the peptide vis-à-vis its corresponding non-labelled peptide. Mass-labelled peptides are particularly useful as positive controls, standards and calibrators in mass spectrometry applications. In particular, peptides including one or more distinct isotopes are chemically alike, separate chromatographically and electrophoretically in the same manner and also ionise and fragment in the same way. However, in a suitable mass analyser such peptides and optionally select fragmentation ions thereof will display distinguishable m/z ratios and may thus be discriminated. Examples of pairs of distinguishable stable isotopes include H and D, $^{12}C$ and $^{13}C$, $^{14}N$ and $^{15}N$ or $^{16}O$ and $^{18}O$. Usually, peptides and proteins of biological samples analysed in the present invention may substantially only contain common isotopes having high prevalence in nature, such as for example H, $^{12}C$, $^{14}N$ and $^{16}O$. In such case, the mass-labelled peptide may be labelled with one or more uncommon isotopes having low prevalence in nature, such as for instance D, $^{13}O$, $^{15}N$ and/or $^{18}O$. It is also conceivable that in cases where the peptides or proteins of a biological sample would include one or more uncommon isotopes, the mass-labelled peptide may comprise the respective common isotope(s).

Isotopically-labelled synthetic peptides may be obtained inter alia by synthesising or recombinantly producing such peptides using one or more isotopically-labelled amino acid substrates, or by chemically or enzymatically modifying unlabelled peptides to introduce thereto one or more distinct isotopes. By means of example and not limitation, D-labelled peptides may be synthesised or recombinantly produced in the presence of commercially available deuterated L-methionine $CH_3-S-CD_2CD_2-CH(NH_2)-COOH$ or deuterated arginine $H_2NC(=NH)-NH-(CD_2)_3-CD(NH_2)-COOH$. It shall be appreciated that any amino acid of which deuterated or $^{15}N-$ or $^{13}C$-containing forms exist may be considered for synthesis or recombinant production of labelled peptides. In another non-limiting example, a peptide may be treated with trypsin in $H_2{}^{16}O$ or $H_2{}^{18}O$, leading to incorporation of two oxygens ($^{16}O$ or $^{18}O$, respectively) at the COOH-termini of said peptide (e.g., US 2006/105415).

Also contemplated is the use of biomarkers, peptides, polypeptides or proteins and fragments thereof as taught herein, optionally comprising a detectable label, as (positive) controls, standards or calibrators in qualitative or quantitative detection assays (measurement methods) of the biomarkers, peptides, polypeptides or proteins and fragments thereof, and particularly in such methods for the diagnosis, prognosis, monitoring and/or screening or as a target for the treatment of solid tumour cancers as taught herein in subjects. The biomarkers, proteins, polypeptides or peptides may be supplied in any form, inter alia as precipitate, vacuum-dried, lyophilisate, in solution as liquid or frozen, or covalently or non-covalently immobilised on solid phase, such as for example, on solid chromatographic matrix or on glass or plastic or other suitable surfaces (e.g., as a part of peptide arrays and microarrays). The peptides may be readily prepared, for example, isolated from natural sources, or prepared recombinantly or synthetically.

Further disclosed are binding agents capable of specifically binding to biomarkers, peptides, polypeptides or proteins and fragments thereof as taught herein. Binding agents as intended throughout this specification may include inter alia an antibody, aptamer, photoaptamer, protein, peptide, peptidomimetic or a small molecule.

The term "specifically bind" as used throughout this specification means that an agent (denoted herein also as "specific-binding agent") binds to one or more desired molecules or analytes substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or more greater, than its affinity for a non-target molecule.

Specific binding agents as used throughout this specification may include inter alia an antibody, aptamer, spiegelmer (L-aptamer), photoaptamer, protein, peptide, peptidomimetic or a small molecule.

Preferably, the agent may bind to its intended target(s) with affinity constant ($K_A$) of such binding $K_A \geq 1\times 10^6$ M−1, more preferably $K_A \geq 1\times 10^7$ M−1, yet more preferably $K_A \geq 1\times 10^8$ M−1, even more preferably $K_A \geq 1\times 10^9$ M−1, and still more preferably $K_A \geq 1\times 10^{10}$ M−1 or $K_A \geq 1\times 10^{11}$ M−1, wherein $K_A=[SBA\_T]/[SBA][T]$, SBA denotes the specific-binding agent, T denotes the intended target. Determination of $K_A$ can be carried out by methods known in the art, such as for example, using equilibrium dialysis and Scatchard plot analysis.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar as they exhibit the desired biological activity (particularly, ability to specifically bind an antigen of interest), as well as multivalent and/or multi-specific composites of such fragments.

The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al (*Nature* (1975) 256:495), or may be made by recombinant DNA methods (e.g., as in U.S. Pat. No. 4,816,567). Monoclonal antibodies may also be isolated from phage antibody libraries using techniques as described by Clackson et al (*Nature* (1991) 352:624-628) and Marks et al (*J. Mol. Biol.* (1991) 222:581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments; diabodies; linear antibodies; single-chain antibody molecules; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., Camelus bactrianus and Camelus dromaderius), llama (e.g., Lama paccos, Lama glama or Lama vicugna) or horse.

A skilled person will understand that an antibody may include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., $K_A$ in the order $1 \geq 10^9$ $M^{-1}$) for their targets. Aptamer production is described inter alia in U.S. Pat. No. 5,270,163; Ellington and Szostak (*Nature* (1990) 346:818-822); Tuerk & Gold (*Science* (1990) 249:505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell (*Trends Biotechnol.* (1995) 13:132-134).

The term "small molecule" refers to compounds, preferably organic compounds, with a size comparable to those organic molecules generally used in pharmaceuticals. The term excludes biological macromolecules (e.g., proteins, nucleic acids, etc.).

Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

Hence, also disclosed are methods for immunising animals, e.g., non-human animals such as laboratory or farm, animals using (i.e., using as the immunising antigen) any one or more (isolated) markers, peptides, polypeptides or proteins and fragments thereof as taught herein, optionally attached to a presenting carrier. Immunisation and preparation of antibody reagents from immune sera is well-known per se and described in documents referred to elsewhere in this specification. The animals to be immunised may include any animal species, preferably warm-blooded species, more preferably vertebrate species, including, e.g., birds, fish, and mammals. Without limitation, the antibodies may be chicken, turkey, goose, duck, guinea fowl, shark, quail or pheasant. Also without limitation, the antibodies may be human, murine (e.g., mouse, rat, etc.), donkey, rabbit, goat, sheep, guinea pig, shark, camel, llama or horse. The term "presenting carrier" or "carrier" generally denotes an immunogenic molecule which, when bound to a second molecule, augments immune responses to the latter, usually through the provision of additional T cell epitopes. The presenting carrier may be a (poly)peptidic structure or a non-peptidic structure, such as inter alia glycans, polyethylene glycols, peptide mimetics, synthetic polymers, etc. Exemplary non-limiting carriers include human Hepatitis B virus core protein, multiple C3d domains, tetanus toxin fragment C or yeast Ty particles.

Immune sera obtained or obtainable by immunisation as taught herein may be particularly useful for generating antibody reagents that specifically bind to any one or more biomarkers, peptides, polypeptides or proteins and fragments thereof disclosed herein.

The binding molecule may labelled with a tag that permits detection with another agent (e.g. with a probe binding partner). Such tags may be, for example, biotin, streptavidin, his-tag, myc tag, maltose, maltose binding protein or any other kind of tag known in the art that has a binding partner. Example of associations which may be utilised in the probe: binding partner arrangement may be any, and includes, for example biotin: streptavidin, his-tag: metal ion (e.g. $Ni^{2+}$), maltose: maltose binding protein.

The binding molecule conjugate may be associated with or attached to a detection agent to facilitate detection. Examples of lab detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. More commonly, the detection agent is a particle. Examples of particles useful in the practice of the invention include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles are colloidal gold particles. Colloidal gold may be made by any conventional means, such as the methods outlined by Frens (*Nature Physical Science* (1973) 241:20). Alternative methods may be described in U.S. Pat. Nos. 5,578,577, 5,141,850; 4,775,636; 4,853,335; 4,859,612; 5,079,172; 5,202,267; 5,514,602; 5,616,467; 5,681,775.

Any existing, available or conventional separation, detection and quantification methods may be used herein to measure the presence or absence (e.g., readout being present vs. absent; or detectable amount vs. undetectable amount) and/or quantity (e.g., readout being an absolute or relative quantity, such as, for example, absolute or relative concentration) of biomarkers, peptides, polypeptides, proteins and/or fragments thereof in samples (any molecules or analytes of interest to be so-measured in samples, including any one or more biomarkers, peptides, polypeptides, proteins and fragments thereof as taught herein, may be herein below referred to collectively as biomarkers).

For example, such methods may include biochemical assay methods, immunoassay methods, mass spectrometry analysis methods, or chromatography methods, or combinations thereof.

The term "immunoassay" generally refers to methods known as such for detecting one or more molecules or analytes of interest in a sample, wherein specificity of an immunoassay for the molecule(s) or analyte(s) of interest is conferred by specific binding between a specific-binding agent, commonly an antibody, and the molecule(s) or analyte(s) of interest. Immunoassay technologies include without limitation direct ELISA (enzyme-linked immunosorbent assay), indirect ELISA, sandwich ELISA, competitive ELISA, multiplex ELISA, radioimmunoassay (RIA), ELISPOT technologies, and other similar techniques known in the art. Principles of these immunoassay methods are known in the art, for example John R. Crowther, "The ELISA Guidebook", 1st ed., Humana Press 2000, ISBN 0896037282.

By means of further explanation and not limitation, direct ELISA employs a labelled primary antibody to bind to and thereby quantify target antigen in a sample immobilised on a solid support such as a microwell plate. Indirect ELISA uses a non-labelled primary antibody which binds to the target antigen and a secondary labelled antibody that recognises and allows the quantification of the antigen-bound primary antibody. In sandwich ELISA the target antigen is captured from a sample using an immobilised 'capture' antibody which binds to one antigenic site within the antigen, and subsequent to removal of non-bound analytes the so-captured antigen is detected using a 'detection' antibody which binds to another antigenic site within said antigen, where the detection antibody may be directly labelled or indirectly detectable as above. Competitive ELISA uses a labelled 'competitor' that may either be the primary antibody or the target antigen. In an example, non-labelled immobilised primary antibody is incubated with a sample, this reaction is allowed to reach equilibrium, and then labelled target antigen is added. The latter will bind to the primary antibody wherever its binding sites are not yet occupied by non-labelled target antigen from the sample. Thus, the detected amount of bound labelled antigen inversely correlates with the amount of non-labelled antigen in the sample. Multiplex ELISA allows simultaneous detection of two or more analytes within a single compartment (e.g., microplate well) usually at a plurality of array addresses (see, for example, Nielsen & Geierstanger (2004) *J. Immunol. Methods* 290:107-20 and Ling et al (2007) *Expert Rev. Mol. Diagn.* 7:87-98 for further guidance). As appreciated, labelling in ELISA technologies is usually by enzyme (such as, e.g., horse-radish peroxidase) conjugation and the end-point is typically colourimetric, chemiluminescent or fluorescent, magnetic, piezo electric, pyroelectric and other.

Radioimmunoassay (RIA) is a competition-based technique and involves mixing known quantities of radioactively-labelled (e.g., $^{125}$I- or $^{131}$I-labelled) target antigen with antibody to said antigen, then adding non-labelled or 'cold' antigen from a sample and measuring the amount of labelled antigen displaced (see, e.g., "An Introduction to Radioimmunoassay and Related Techniques", by Chard T, ed., Elsevier Science 1995, ISBN 0444821198 for guidance).

Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), are useful herein. Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann (1990) *Methods Enzymol.* 193:455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of biomarkers by mass spectrometry may involve multiple reaction monitoring (MRM), such as described among others by Kuhn et al 2004 (*Proteomics* 4:1175-86). MS peptide analysis methods may be advantageously combined with upstream peptide or protein separation or fractionation methods, such as for example with the chromatographic and other methods described herein below.

Chromatography may also be used for measuring biomarkers. As used herein, the term "chromatography" encompasses methods for separating chemical substances, referred to as such and vastly available in the art. In a preferred approach, chromatography refers to a process in which a mixture of chemical substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography as used herein may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilised metal affinity chromatography, and the like.

Chromatography, including single-, two- or more-dimensional chromatography, may be used as a peptide fractionation method in conjunction with a further peptide analysis method, such as for example, with a downstream mass spectrometry analysis as described elsewhere in this specification.

Further peptide or polypeptide separation, identification or quantification methods may be used, optionally in conjunction with any of the above described analysis methods, for measuring biomarkers in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

The level of biomarkers at the RNA level may be detected using standard quantitative RNA measurement tools known in the art. Non-limiting examples include hybridization-based analysis, microarray expression analysis, digital gene expression (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing and sequencing by synthesis.

The various aspects and embodiments taught herein may further rely on comparing the quantity of biomarkers measured in samples and the measurement or score of parameters in patients with reference values, wherein said reference values represent known diagnoses and/or prognoses of solid tumour cancers taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values may represent the diagnosis of a solid tumour cancer as taught herein vs. the diagnosis of no such cancer (such as, e.g., the diagnosis of healthy, or recovered from the cancer, etc.). In another example, distinct reference values may represent the diagnosis of a solid tumour cancer of varying severity.

In yet another example, distinct reference values may represent a good prognosis for a solid tumour cancer as taught herein vs. a poor prognosis for the cancer. In a further example, distinct reference values may represent varyingly favourable or unfavourable prognoses for such a cancer.

Such comparison may generally include any means to determine the presence or absence of at least one difference and optionally of the size of such difference between values being compared. A comparison may include a visual inspection, an arithmetical or statistical comparison of measurements. Such statistical comparisons include, but are not limited to, applying a rule.

Reference values may be established according to known procedures previously employed for other biomarkers and parameters. For example, a reference value may be established in an individual or a population of individuals, ideally characterised by being free from or having no solid tumour. Such population may comprise without limitation ≥2, ≥10, ≥100, or even several hundreds or more individuals.

In an embodiment, reference value(s) as intended herein may convey absolute quantities of the biomarkers, peptides, polypeptides, proteins or a fragment thereof as intended herein. In another embodiment, the quantity of the biomarkers, peptides, polypeptides, proteins or a fragment thereof in a sample from a tested subject may be determined directly relative to the reference value (e.g., in terms of increase or decrease, or fold-increase or fold-decrease). Advantageously, this may allow the comparison of the quantity of the biomarkers, peptides, polypeptides, proteins or a fragment thereof in the sample from the subject with the reference value (in other words to measure the relative quantity of the biomarkers, peptides, polypeptides, proteins or a fragment thereof in the sample from the subject vis-à-vis the reference value) without the need first to determine the respective absolute quantities of the biomarkers, peptides, polypeptides, proteins or a fragment thereof.

The expression level or presence of a biomarker in a sample of a patient may sometimes fluctuate, i.e. increase or decrease significantly without change (appearance of, worsening or improving) of symptoms. In such an event, the marker change precedes the change in symptoms and becomes a more sensitive measure than symptom change. Therapeutic intervention may be initiated earlier and be more effective than waiting for deteriorating symptoms.

Also disclosed is a method or algorithm for determining a significant change in the level of any one or more of the markers as taught herein or a fragment thereof in a certain patient, which is indicative for change (worsening or improving) in clinical status. In addition, the invention allows establishing the diagnosis that the subject is recovering or has recovered from a solid tumour as taught herein.

The various aspects and embodiments taught herein may further entail finding a deviation or no deviation between the quantity or level of ATP11B (and optionally S100A11) gene expression and/or the quantity or concentration of protein or peptides resulting from ATP11B (and optionally S100A11) gene translation as taught herein measured in a sample from a subject and a given reference value.

A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\geq 1 \times SD$ or $\geq 2 \times SD$, or $\geq 1 \times SE$ or $\geq 2 \times SE$). Deviation may also refer to a value falling outside of a reference range defined by values in a given population (for example, outside of a range which comprises $\geq 40\%$, $\geq 50\%$, $\geq 60\%$, $\geq 70\%$, $\geq 75\%$ or $\geq 80\%$ or $\geq 85\%$ or $\geq 90\%$ or $\geq 95\%$ or even $\geq 100\%$ of values in the population).

In a further embodiment, a deviation may be concluded if an observed alteration is beyond a given threshold or cut-off. Such threshold or cut-off may be selected as generally known in the art to provide for a chosen sensitivity and/or specificity of the diagnosis and/or prognosis methods, e.g., sensitivity and/or specificity of at least 50%, or at least 60%, or at least 70%, or at least 80%, or at least 85%, or at least 90%, or at least 95%.

The present invention further provides kits or devices as set forth above for the diagnosis, prognosis and/or monitoring of a solid tumour cancer as taught herein comprising means for detecting the quantity or level of ATP11B (and optionally S100A11) gene expression and/or the quantity or concentration of protein or peptides resulting from ATP11B (and optionally S100A11) gene translation in a sample of a patient. In a preferred embodiment, such a kit or kits may be used in clinical settings or at home. The kit may be used for diagnosing a solid tumour cancer, for monitoring the effectiveness of treatment of a subject suffering from a solid tumour cancer, or for preventive screening of subjects for the occurrence of solid tumour cancer in a subject.

In a clinical setting, the kit or device may be in the form of a bed-side device or in an emergency team setting, e.g. as part of the equipment of an ambulance or other moving emergency vehicle or team equipment or as part of a first-aid kit. The diagnostic kit or device may assist a medical practitioner, a first aid helper, or nurse to decide whether the patient under observation is developing a solid tumour cancer as taught herein, after which appropriate action or treatment may be performed. For example, appropriate action may be sending the patient for further testing to confirm the diagnosis and elucidate the extent and location of the solid tumour.

A home-test kit gives the patient a readout which he/she may communicate to a medicinal practitioner, a first aid helper or to the emergency department of a hospital, after which appropriate action can be taken. Such a home-test device is of particular interest for people having either a history of, or who are at risk of suffering from a solid tumour cancer as taught herein.

Non-limiting examples are: systems comprising specific binding molecules for the requisite biomarker(s) attached to a solid phase, e.g. lateral flow strips or dipstick devices and the like well known in the art. One non-limiting example to perform a biochemical assay is to use a test-strip and labelled antibodies which combination does not require any washing of the membrane. The test strip is well known, for example, in the field of pregnancy testing kits where an anti-hCG antibody is present on the support, and is carried complexed with hCG by the flow of urine onto an immobilised second antibody that permits visualisation. Other non-limiting examples of such home test devices, systems or kits can be found for example in the following U.S. Pat. Nos. 6,107,045, 6,974,706, 5,108,889, 6,027,944, 6,482,156, 6,511,814, 5,824,268, 5,726,010, 6,001,658 or U.S. Patent Application numbers 2008/0090305 or 2003/0109067. In a preferred embodiment, the invention provides a lateral flow device or dipstick. Such dipstick comprises a test strip allowing migration of a sample by capillary flow from one end of the strip where the sample is applied to the other end of such strip where presence of an analyte in said sample is measured. In another embodiment, the invention provides a device comprising a reagent strip. Such reagent strip comprises one or more test pads which, when wetted with the sample, provide a colour change in the presence of an analyte and/or indicate the concentration of the biomarker in the sample.

In order to obtain a semi-quantitative test strip in which only a signal is formed once the level of the requisite biomarker(s) in the sample is higher than a certain predetermined threshold level or value, a predetermined amount of fixed capture antibodies for the biomarker(s) may be present on the test strip. This enables the capture of a certain amount of the biomarker(s) present in the sample, corresponding to the threshold level or value as predetermined. The remaining amount of biomarker(s) (if any) bound by e.g. a conjugated or labelled binding molecules may then be allowed to migrate to a detection zone which subsequently only produces a signal if the level of the biomarker(s) in the sample is higher than the predetermined threshold level or value.

Another possibility to determine whether the amount of any the requisite biomarker(s) in the sample is below or above a certain threshold level or value, is to use a primary capturing antibody capturing all said biomarker(s) present in the sample, in combination with a labelled secondary antibody, developing a certain signal or colour when bound to the solid phase. The intensity of the colour or signal may then either be compared to a reference colour or signal chart indicating that when the intensity of the signal is above a certain threshold signal, the test is positive. Alternatively, the amount or intensity of the colour or signal may be measured with an electronic device comprising e.g. a light absorbance sensor or light emission meter, resulting in a numerical value of signal intensity or colour absorbance formed, which may then be displayed to the subject in the form of a negative result if said numerical value is below the threshold value or a positive result if said numerical value is above the threshold value. This embodiment is of particular relevance in monitoring the level of said biomarker(s) in a patient over a period of time.

The reference value or range may e.g. be determined using the home device in a period wherein the subject is free of a solid tumour cancer, giving the patient an indication of his/her base-line level of the biomarker(s). Regularly use of a home test device will thus enable a subject to notice a sudden change in levels of the one or more biomarker(s) compared to a base-line level, which enable him/her to contact a medical practitioner.

Alternatively, the reference value may be determined in the subject suffering from a solid tumour cancer as taught herein, which then indicates his/her personal "risk level" for the biomarker(s), i.e. the level of the biomarker(s) which indicates he/she is or will soon be exposed to a solid tumour. This risk level is interesting for monitoring the disease progression or for evaluating the effect of the treatment.

Furthermore, the reference value or level may be established through combined measurement results in subjects with highly similar phenotypes (e.g. all having no solid tumour cancers as taught herein).

Non-limiting examples of semi-quantitative tests known in the art, the principle of which may be used for the home test device according to the present invention are the HIV/AIDS test or Prostate Cancer tests sold by Sanitoets™. The home prostate test is a rapid test intended as an initial semi-quantitative test to detect PSA blood levels higher than 4 ng/ml in whole blood. The typical home self-test kit comprises the following components: a test device to which the blood sample is to be administered and which results in a signal when the protein level is above a certain threshold level, an amount of diluent e.g. in dropper pipette to help the transfer of the analytes (i.e. the protein of interest) from the sample application zone to the signal detection zone, optionally an empty pipette for blood specimen collection, a finger pricking device, optionally a sterile swab to clean the area of pricking and instructions of use of the kit.

Similar tests are also known for e.g. breast cancer detection and CRP-protein level detection in view of cardiac risk home tests. The latter test encompasses the sending of the test result to a laboratory, where the result is interpreted by a technical or medical expert. Such telephone or internet based diagnosis of the patient's condition is of course possible and advisable with most of the kits, since interpretation of the test result is often more important than conducting the test. When using an electronic device as mentioned above which gives a numerical value of the level of protein present in the sample, this value may of course easily be communicated through telephone, mobile telephone, satellite phone, E-mail, internet or other communication means, warning a hospital, a medicinal practitioner or a first aid team that a person is, or may be at risk of, suffering from the disease or condition as taught herein. A non-limiting example of such a system is disclosed in U.S. Pat. No. 6,482,156.

The presence and/or concentration of biomarker(s) in a sample may be measured by surface plasmon resonance (SPR) using a chip having binding molecule for said biomarker(s) immobilized thereon, fluorescence resonance energy transfer (FRET), bioluminescence resonance energy transfer (BRET), fluorescence quenching, fluorescence polarization measurement or other means known in the art. Any of the binding assays described may be used to determine the presence and/or concentration of any biomarker(s) in a sample. To do so, binding molecules for the biomarker(s) are reacted with a sample, and the concentration of the biomarker(s) is measured as appropriate for the binding assay being used. To validate and calibrate an assay, control reactions using different concentrations of standard biomarker(s) and/or binding molecule therefore may be performed. Where solid phase assays are employed, after incubation, a washing step is performed to remove unbound markers. Bound biomarker is measured as appropriate for the given label (e.g., scintillation counting, fluorescence, antibody-dye etc.). If a qualitative result is desired, controls and different concentrations may not be necessary. Of course, the roles of said biomarker(s) and binding molecule may be switched; the skilled person may adapt the method so binding molecule is applied to sample, at various concentrations of sample.

A "binding molecule for any one or more markers as taught herein" is any substance that binds specifically to any one or more markers as taught herein. Examples of a binding molecule for any one or more markers as taught herein or a fragment thereof, includes, but is not limited to an antibody, a polypeptide, a peptide, a lipid, a carbohydrate, a nucleic acid, peptide-nucleic acid, small molecule, small organic molecule, or other drug candidate. A binding molecule for any one or more markers as taught herein or a fragment thereof may be natural or synthetic compound, including, for example, synthetic small molecule, compound contained in extracts of animal, plant, bacterial or fungal cells, as well as conditioned medium from such cells. Alternatively, binding molecule for any one or more markers as taught herein or a fragment thereof may be an engineered protein having binding sites for any one or more markers as taught herein or a fragment thereof. According to an aspect of the invention, a binding molecule for any one or more markers as taught herein or a fragment thereof binds specifically to any one or more markers as taught herein or a fragment thereof with an affinity better than $10^{-6}$ M. A suitable binding molecule for any one or more markers as taught herein or a fragment thereof may be determined from its binding with a standard sample of any one or more markers as taught herein or a fragment thereof. Methods for determining the binding between binding molecules for any one or more markers as taught herein or a fragment thereof and any one or more markers as taught herein or a fragment thereof are known in the art. As used herein, the term antibody includes, but is not limited to, polyclonal antibodies, monoclonal antibodies, humanised or chimeric antibodies, engineered antibodies, and biologically functional antibody fragments (e.g. scFv, nanobodies, Fv, etc) sufficient for binding of the antibody fragment to the protein. Such antibody may be commercially available antibody against any one or more markers as taught herein or a fragment thereof, such as, for example, a mouse, rat, human or humanised monoclonal antibody.

In a preferred embodiment, the binding molecule or agent is capable of binding both the mature membrane- or cell-bound protein or fragment of any one or more markers as taught herein or a fragment thereof. In a more preferred embodiment, the binding agent or molecule is specifically binding or detecting the soluble form, preferably the plasma circulating form of any one or more markers as taught herein or a fragment thereof.

According to one aspect of the invention, the binding molecule for any one or more markers as taught herein or a fragment thereof is labelled with a tag that permits detection with another agent (e.g. with a probe binding partner). Such tags can be, for example, biotin, streptavidin, his-tag, myc tag, maltose, maltose binding protein or any other kind of tag known in the art that has a binding partner. Example of associations which can be utilised in the probe: binding partner arrangement may be any, and includes, for example biotin: streptavidin, his-tag: metal ion (e.g. $Ni^{2+}$), maltose: maltose binding protein.

The specific-binding agents, peptides, polypeptides, proteins, biomarkers etc. in the present kits may be in various forms, e.g., lyophilised, free in solution or immobilised on a solid phase. They may be, e.g., provided in a multi-well plate or as an array or microarray, or they may be packaged separately and/or individually. The may be suitably labelled as taught herein. Said kits may be particularly suitable for performing the assay methods of the invention, such as, e.g., immunoassays, ELISA assays, mass spectrometry assays, and the like.

The term "modulate" generally denotes a qualitative or quantitative alteration, change or variation specifically encompassing both increase (e.g., activation) or decrease (e.g., inhibition), of that which is being modulated. The term encompasses any extent of such modulation.

For example, where modulation effects a determinable or measurable variable, then modulation may encompass an increase in the value of said variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of said variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation.

Preferably, modulation of the activity and/or level of intended target(s) (e.g., any one or more markers, nucleic acids, peptides, polypeptides or proteins as taught herein) may be specific or selective, i.e., the activity and/or level of intended target(s) may be modulated without substantially altering the activity and/or level of random, unrelated (unintended, undesired) targets.

Reference to the "activity" of a target may generally encompass any one or more aspects of the biological activity of the target, such as without limitation any one or more aspects of its biochemical activity, enzymatic activity, signalling activity and/or structural activity, e.g., within a cell, tissue, organ or an organism.

In the context of therapeutic or prophylactic targeting of a target, the reference to the "level" of a target may preferably encompass the quantity and/or the availability (e.g., availability for performing its biological activity) of the target, e.g., within a cell, tissue, organ or an organism.

For example, the level of a target may be modulated by modulating the target's expression and/or modulating the expressed target. Modulation of the target's expression may be achieved or observed, e.g., at the level of heterogeneous nuclear RNA (hnRNA), precursor mRNA (pre-mRNA), mRNA or cDNA encoding the target. By means of example and not limitation, decreasing the expression of a target may be achieved by methods known in the art, such as, e.g., by transfecting (e.g., by electroporation, lipofection, etc.) or transducing (e.g., using a viral vector) a cell, tissue, organ or organism with an antisense agent, such as, e.g., antisense DNA or RNA oligonucleotide, a construct encoding the antisense agent, or an RNA interference agent, such as siRNA or shRNA, or a ribozyme or vectors encoding such, etc. By means of example and not limitation, increasing the expression of a target may be achieved by methods known in the art, such as, e.g., by transfecting (e.g., by electroporation, lipofection, etc.) or transducing (e.g., using a viral vector) a cell, tissue, organ or organism with a recombinant nucleic acid which encodes said target under the control of regulatory sequences effecting suitable expression level in said cell, tissue, organ or organism. By means of example and not limitation, the level of the target may be modulated via alteration of the formation of the target (such as, e.g., folding, or interactions leading to formation of a complex), and/or the stability (e.g., the propensity of complex constituents to associate to a complex or disassociate from a complex), degradation or cellular localisation, etc. of the target.

The term "antisense" generally refers to a molecule designed to interfere with gene expression and capable of specifically binding to an intended target nucleic acid sequence. Antisense agents typically encompass an oligonucleotide or oligonucleotide analogue capable of specifically hybridising to the target sequence, and may typically comprise, consist essentially of or consist of a nucleic acid sequence that is complementary or substantially complementary to a sequence within genomic DNA, hnRNA, mRNA or cDNA, preferably mRNA or cDNA corresponding to the target nucleic acid. Antisense agents suitable herein may typically be capable of hybridising to their respective target at high stringency conditions, and may hybridise specifically to the target under physiological conditions.

The term "ribozyme" generally refers to a nucleic acid molecule, preferably an oligonucleotide or oligonucleotide analogue, capable of catalytically cleaving a polynucleotide.

Preferably, a "ribozyme" may be capable of cleaving mRNA of a given target protein, thereby reducing translation thereof. Exemplary ribozymes contemplated herein include, without limitation, hammer head type ribozymes, ribozymes of the hairpin type, delta type ribozymes, etc. For teaching on ribozymes and design thereof, see, e.g., U.S. Pat. Nos. 5,354,855, 5,591,610, Pierce et al (*Nucleic Acids Res.* (1998) 26:5093-5101), Lieber et al (*Mol. Cell. Biol.* (1995) 15:540-551), and Benseler et al (*J. Am. Chem. Soc.* (1993) 115: 8483-8484).

"RNA interference" or "RNAi" technology is routine in the art and suitable RNAi agents intended herein may include inter alia short interfering nucleic acids (siNA), short interfering RNA (siRNA), double-stranded RNA (dsRNA), micro-RNA (miRNA), and short hairpin RNA (shRNA) molecules as known in the art. For teaching on RNAi molecules and design thereof, see inter alia Elbashir et al (*Nature* (2001) 411:494-501), Reynolds et al (*Nature Biotechnol.* (2004) 22:326-30), http://rnaidesigner.invitrogen.com/rnaiexpress, Wang & Mu (*Bioinformatics* (2004) 20:1818-20), Yuan et al (*Nucleic Acids Res.* (2004) 32 (Web Server issue):W130-4), Sohail ("Gene Silencing by RNA Interference: Technology and Application" (2004) 1st ed., CRC, ISBN 0849321417), Schepers ("RNA Interference in Practice: Principles, Basics, and Methods for Gene Silencing in *C. elegans, Drosophila*, and Mammals", (2005) 1st ed., Wiley-VCH, ISBN 3527310207), and Engelke and Rossi ("Methods in Enzymology, Volume 392: RNA Interference", (2005) 1st ed., Academic Press, ISBN 0121827976).

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colourants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

The present active substances (agents) may be used alone or in combination with any therapies known in the art for the disease and conditions as taught herein ("combination therapy"). Combination therapies as contemplated herein may comprise the administration of at least one active substance of the present invention and at least one other pharmaceutically or biologically active ingredient. Said present active substance(s) and said pharmaceutically or biologically active ingredient(s) may be administered in either the same or different pharmaceutical formulation(s), simultaneously or sequentially in any order.

The dosage or amount of the present active substances (agents) used, optionally in combination with one or more other active compound to be administered, depends on the individual case and is, as is customary, to be adapted to the individual circumstances to achieve an optimum effect. Thus, it depends on the nature and the severity of the disorder to be treated, and also on the sex, age, body weight, general health, co-morbidity, other medication, diet, mode and time of administration, and individual responsiveness of the human or animal to be treated, on the route of administration, efficacy, metabolic stability and duration of action of the compounds used, on whether the therapy is acute or chronic or prophylactic, or on whether other active compounds are administered in addition to the agent(s) of the invention.

Without limitation, depending on the type and severity of the disease, a typical daily dosage might range from about 1 µg/kg to 100 mg/kg of body weight or more, depending on the factors mentioned above. For repeated administrations over several days or longer, depending on the condition, the treatment is sustained until a desired suppression of disease symptoms occurs. A preferred dosage of the active substance of the invention may be in the range from about 0.05 mg/kg to about 10 mg/kg of body weight. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every two or three weeks.

As used herein, a phrase such as "a subject in need of treatment" includes subjects that would benefit from treatment of a given disease or condition as taught herein. Such subjects may include, without limitation, those that have been diagnosed with said condition, those prone to contract or develop said condition and/or those in whom said condition is to be prevented.

The terms "treat" or "treatment" encompass both the therapeutic treatment of an already developed disease or condition (medically or surgically), as well as prophylactic or preventative measures, wherein the aim is to prevent or lessen the chances of incidence of an undesired affliction, such as to prevent the chances of contraction and progression of a disease or condition as taught herein. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" may also mean prolonging survival as compared to expected survival if not receiving treatment.

The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically effective doses for compounds disclosed herein.

Figure 2:
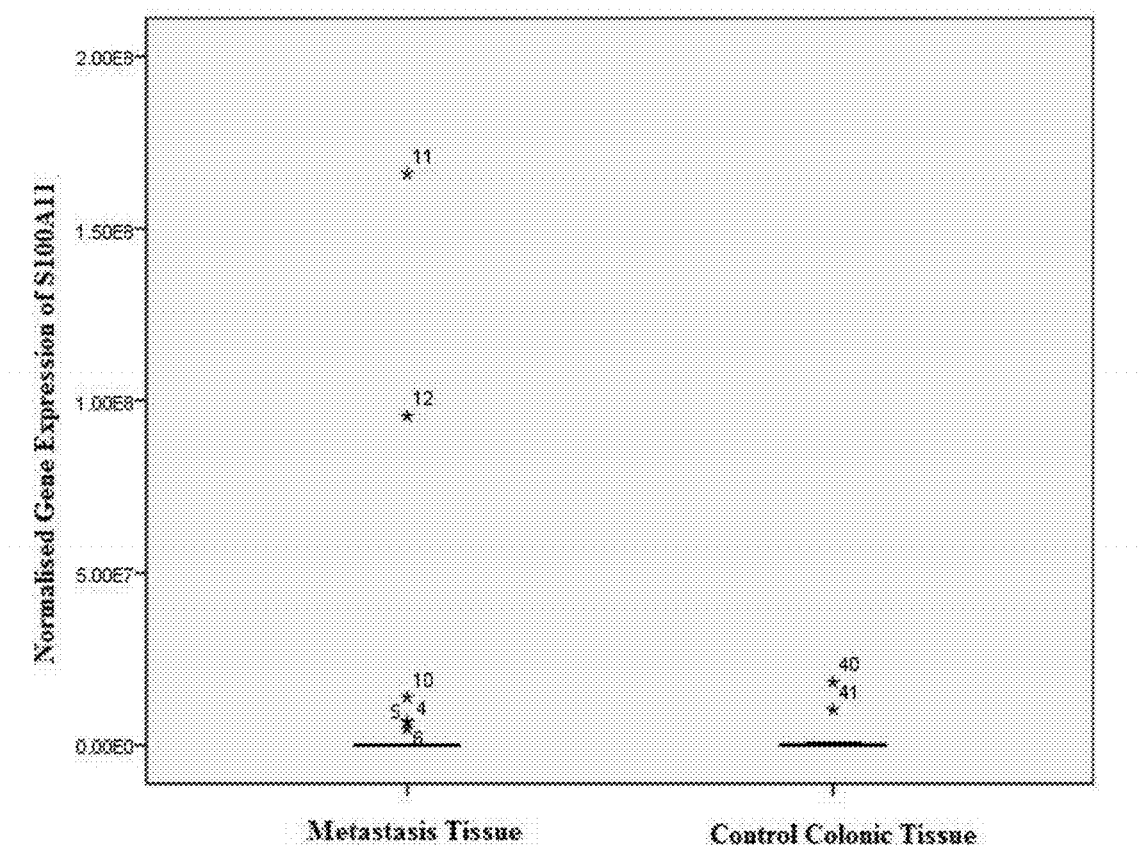

The above aspects and embodiments are further supported by the following non-limiting example in which:

FIG. 1 is a Box-and-Whisker plot of normalised gene expression of ATP11B in metastasis and control colonic tissue analysed by RT-PCR (SPSS software version 18), and FIG. 2 is a Box-and-Whisker plot of normalised gene expression of S100A11 in metastasis and control colonic tissue analysed by RT-PCR (SPSS software version 18).

PATIENTS AND METHODS

Thirty three patients, who underwent liver resection for colorectal liver metastases (CRLM), were recruited prospectively. Patients' demographics, neo-adjuvant chemotherapy, peri-operative outcomes and long term follow-up were recorded. Long term survival was analysed using the Kaplan-Meier technique. Samples of liver parenchyma, 'halo' and colorectal cancer metastasis were retrieved from the resected liver specimens immediately following surgery. Samples of colonic mucosa were retrieved from unrelated patients (n=10). RNA was extracted, hybridised with reference RNA, labelled and applied to c-DNA microarrays (Agilent®).

The gene expression profiles from all samples were analysed by microarray analysis using GeneSpring (X) and MetaCore (GeneGo) as set out above and compared between the four tissue types. The gene expression profiles of each tissue were analysed according to particular conditions, including neo-adjuvant chemotherapy exposure, intra-operative Pringle manoeuvre, systemic ischaemia, pre-operative CEA levels, number and size of CRLM and resection margin status. Gene expression profiles were also compared to a universal human reference RNA (Agilent Technologies)

Statistical analyses were undertaken using GeneSpring (X) and MetaCore (GeneGo) software and p<0.05 and >2 fold change were considered significant.

Two hundred and forty consecutive patients who underwent liver resection for CRLM over a twelve year period were recruited retrospectively and grouped according to those who received neo-adjuvant chemotherapy and those who did not. The samples of resected liver were studied using standard histopathological techniques, and evidence of hepatocellular injury, steatosis and steatohepatitis were determined using the scoring system designed by Kleiner et al. Peri-operative morbidity, 90-day mortality and long term survival were analysed and correlated to neo-adjuvant chemotherapy exposure and severity of hepatocellular injury.

Statistical analyses were undertaken using SPSS (v18). $X^2$ and Fisher's exact tests were used to compare categorical variables and the Kruskal-Wallis test was used to compare continuous variables. Long term survival curves using the Kaplan-Meier technique were constructed. P<0.05 was considered statistically significant.

A power calculation was undertaken to predict the least number of patients required for recruitment in order to obtain statistically significant changes between samples. The theoretical limit based on T-test simulations was 10 patients. The pre-study aim was to recruit 30 patients.

Results

Clustering analysis was undertaken to determine the general differences between the study tissues. 'Halo', liver parenchyma, colorectal cancer metastasis and control colonic tissue were clustered using hierarchical clustering, Pearson's absolute distance metric and the centroid linkage rule. Class prediction models were constructed using GeneSpring X software to determine whether the gene expression profiles may be used to predict identification of distinct tissue types. The Naive Bayesian model of tissue type prediction based on gene expression was used. Prediction accuracy was determined with N-fold validation, with number of folds=3 and number of repeats=1 (Komori T et al (*International Journal of Oncology* (2008); 32:367-375; Takemasa I et al (*Biochem. Biophys. Res. Commun.* (2001) 285:1244-1249)). This method predicted the probability that a sample belonged to a particular class according to the gene expression profile. However, this assumed that the affect of an attribute on a specific class was independent of the value of other attributes. This was known as the class conditional independence, and was measured by the following algorithm;

$$P(X \mid C_i) = \prod_{k=1}^{n} P(x_k \mid C_i)$$

Given an unknown data sample X the classifier predicted that X belonged to the class having the highest posterior probability (P), conditioned on X, X was then assigned to class $C_i$.'

The mean normalised expression of ATP11B in metastasis tissue was $3.48 \times 10^9$ (range, $9.12 \times 10^9$-$6.91 \times 10^7$; SE $8.39 \times 10^8$; 95% CI, $1.67 \times 10^9$-$5.28 \times 10^9$) and control colonic tissue was $2.36 \times 10^8$ (range, $6.17 \times 10^8$-$6.45 \times 10^7$; SE $5.25 \times 10^7$; 95% CI, $1.15 \times 10^8$-$3.57 \times 10^8$; p=0.001). Thus, ATP11B expression >1.48 was able to distinguish between metastasis and other tissue types with an accuracy of 100%, as well as distinguishing between tumour and non-tumour tissue with an accuracy of 100%.

Regarding S100A11 (calgizzarin), the mean normalised expression in metastasis tissue was $1.08 \times 10^7$ (range, $1.16 \times 10^{-17}$-$1.66 \times 10^8$; SE $6.94 \times 10^6$; 95% CI, $-3.39 \times 10^6$ to $2.51 \times 10^7$) and the mean normalised expression in control colonic tissue was $2.02 \times 10^6$ (range, $6.72 \times 10^{-15}$-$1.82 \times 10^7$; SE $8.47 \times 10^5$; 95% CI, $-4.41 \times 10^5$ to $3.06 \times 10^6$; p=0.013). The significant up regulation of calgizzarin (p<0.05) allowed for the distinction between metastasis and all other tissue types in the study with an accuracy of 96.7%, as well as between tumour and non-tumour tissue with the same accuracy.

Discussion

ATP11B is a P-type ATPase and is considered to have a role in aminophospholipid transport, ATP biosynthesis, purine ribonucleoside triphosphate biosynthetic process and lipid transport (Nesbit et al (2004) *Genomics* 84:1060-1070).

Significantly altered expression of ATP11B has not previously been linked to metastatic colonic cancer. It is possible that its significant up regulation may be related to Helicase-like transcription factor (HLTF) expression, as seen in a proportion of primary colonic cancer cell line studies, thus increasing chromatin remodelling and promoting cancer propagation and survival (Moinova et al (2002) *Proc. Natl. Acad. Sci. U.S.A.* 99:4562-4567).

ATP11B has been described as a member of the sub-family of adenosine-triphosphatases (ATPases), which behave as trans-bilayer amphipathic transporters (Nesbit et al supra). This sub-family includes ATP11A, ATP11B and ATP110 (Nesbit et al supra; Halleck et al (2009) *Genome Res.* 8:354-361). However, Nesbit et al (supra) showed that the structure of ATP11A is closely related to that of ATP110 but less so compared with ATP11B. ATP11B has been linked to chromosome 3q26 (Nesbit et al supra; Halleck et al supra; Hewetson et al (2008) *Mol. Cell Endocrinol.* 292:79-86). In the past, its location, and therefore mutation or deletion, have been linked to SOX2. SOX genes encode a family of transcription factors that bind to the minor groove in DNA and mutation and deletion of these have been linked to rare structural eye malformations including anophthalmia and microphthalmia (Drogemuller et al (2004) *International Society for Animal Genetics* 35:462-504).

Calgizzarin, or calcium binding protein A11 (gene=S100A11) is a downstream target of TGFβ and has been described as a cellular division process protein, negatively regulating cell proliferation (Chang et al (2007) *Am. J. Physiol. Cell Physiol.* 292:1417-1430; DeVries et al (1989) *Cell Calcium Metabolism*, Ed. Gary Fiskum, Springer, ISBN: 978-1-4684-5600-4 p.427-437; Todoroki et al (1991) *J. Biol. Chem.* 266:18668-18673; Marenholz et al (2004) *Biochem. Biophys. Res. Commun.* 322:1111-1122).

S100A11, also called calgizzarin, was first described in 1989 by DeVries et al (supra) and is a one of the 20 identified members of the S100 protein family (Chang et al supra; Todoroki et al supra; Marenholz et al supra). S100 are small acidic proteins of 10-12 kDa which contain two distinct binding domains, found on the 1q21 chromosomal locus (Chang et al supra; Marenholz et al supra). S100A11 is homodimeric with two calcium binding sites per 11,282-Da monomer. By binding calcium, S100A11 exposes a hydrophobic surface which subsequently interacts with the target peptide (Schonekess and Walsh M P (1997). *Biochem. Cell Biol.* 75:771-775; Allen et al (1996) *Biochem. Cell Biol.* 74:687-694), allowing a large number of intra- and extracellular functions to be undertaken. S100A11 has been shown to interact with actin, transglutaminase, zinc ($Zn^{2+}$), $Cu^{2+}$ and S100B (Chang et al supra; Marenholz et al supra; Ruse et al (2001) *Biochemistry* 40:3167-3173.; Zeng et al (1993) *Int. J. Biochem.* 25:1019-1027). Calcium ions ($Ca^{2+}$) are intercellular messengers that mediate extracellular signalling, influencing cell growth and differentiation, cell cycle regulation, motility, mitogenesis and metabolism in a wide range of tissue types (Chang et al supra; Marenholz et al supra).

Altered levels of S100 proteins have been associated with malignant change, neurodegenerative disorders, inflammatory disorders and cardiomyopathy (Chang et al supra; Marenholz et al supra). Several members of the S100 family of proteins have been linked to specific disorders, including S100A2 (non-small cell lung cancer, gastric cancer, lymphoma; Marenholz et al supra; El-Rifai et al (2002) *Cancer Res.* 62:6823-6826; Nagy et al (2002) *Histol. Histopathol.* 17:123-130; Wicki et al (1997) *Cell Calcium* 22:243-254), S100A4 (breast cancer), S100A6 (breast cancer, pancreatic cancer), S100P (breast cancer, pancreatic cancer) and S100B (Marenholz et al supra). These proteins may potentially act as tumour suppressors or promoters and increased of expression of S100A2 and S100A4 have been associated with poor cancer related survival. S100A4 has been shown to trigger pro-metastatic cascades in the extra-cellular space surrounding tumour cells (Marenholz et al supra).

CONCLUSION

The prediction model and cluster analyses showed that significant up regulation of ATP11B independently differentiated metastasis from non-malignant malignant tissues with 100% of cases, in this large yet finite sample size. Furthermore, these data showed that significant up regulation of S100A11 differentiated metastasis from non-malignant tissues with 96.7% accuracy.

The invention claimed is:

1. A method for the diagnosis and/or prognosis of colorectal cancer, in a subject, wherein the method comprises:
   (i) measuring the level of ATP11B gene expression and/or the quantity protein or peptides resulting from ATP11B gene translation in a biological sample from the subject, and
   (ii) comparing the level or quantity measured in (i) with a reference value of the level of gene expression or quantity of proteins or peptides resulting from ATP11B gene translation, wherein the reference value represents a constitutive level of the gene expression and/or translation;

wherein either:
   a) gene expression level or protein/peptide quantity at least about 40% (about 1.4-fold or more) above the reference value is indicative of a solid colorectal tumor, or
   b) a gene transcription measurement or protein/peptide quantity substantially at or similar to the reference value indicates that no colorectal cancer tumor is present, and
   (iii) treating the subject identified in (ii)(a) as having a solid colorectal tumor by administering radiotherapy or chemotherapy or carrying out surgery, or a combination thereof.

2. The method according to claim 1, wherein the method further comprises measuring the level of S100A11 gene expression and/or the quantity protein or peptides resulting from S100A11 gene translation and the quantity measured is compared with a reference value of the level of gene expression or quantity of proteins or peptides resulting from S100A11 gene translation, wherein the reference value represents a constitutive level of the gene expression and/or translation.

3. The method according to claim 1, wherein the reference value(s) is obtained from a population that is free from a colorectal cancer.

4. A method for treating colorectal cancer in a subject in need of said treatment, the method comprising:
   a) identifying the subject as in need of treatment for colorectal cancer by a method comprising:
      (i) measuring the level of ATP11B gene expression and/or the quantity protein or peptides resulting from ATP11B gene translation in a biological sample from the subject, and
      (ii) comparing the level or quantity measured in (i) with a reference value of the level of gene expression and/or the quantity of proteins or peptides resulting from ATP11B gene translation, wherein the reference value represents a constitutive level of the gene expression and/or translation;

wherein a) an increased gene expression level or protein/peptide quantity at least about 40% (about 1.4-fold or more) above the reference value is indicative of a colorectal cancer tumor and identifies the subject as in need of treatment, and
   b) treating the subject identified as in need of treatment by administering radiotherapy or chemotherapy or carrying out surgery, or a combination thereof.

5. The method according to claim 4, wherein the method further comprises measuring the level of S100A11 gene expression and/or the quantity protein or peptides resulting from S100A11 gene translation and the quantity measured is compared with a reference value of the level of gene expression or quantity of proteins or peptides resulting from S100A11 gene translation, wherein the reference value represents a constitutive level of the gene expression and/or translation.

6. The method according to claim 1, wherein the protein or peptides resulting from ATP11B gene translation is a P-type ATPase.

7. The method according to claim 6, wherein the P-type ATPase is Probable phospholipid-transporting ATPase IF.

8. The method according to claim 2, wherein the protein or peptides resulting from S100A11 gene translation is S100 calcium binding protein A11 (calgizzarin).

9. The method according to claim 1, wherein the biological sample is blood, plasma, serum, saliva or a tissue biopsy.

10. The use according to claim 1, wherein the level quantity of the one or more markers, is measured using an immunoassay technology, a mass spectrometry analysis method, a chromatography method, or a combination of such methods.

11. The method according to claim 1, wherein the measuring step is performed by an immunoassay technology, a mass spectrometry analysis method, a chromatography method, or a combination of such methods.

12. The method according to claim 4, wherein the protein or peptides resulting from ATP11B gene translation is a P-type ATPase.

13. The method according to claim 12, wherein the P-type ATPase is Probable phospholipid-transporting ATPase IF.

14. The method according to claim 5, wherein the protein or peptides resulting from S100A11 gene translation is S100 calcium binding protein A11 (calgizzarin).

15. The method according to claim 4, wherein the biological sample is blood, plasma, serum, saliva or a tissue biopsy.

16. The method according to claim 4, wherein the measuring step is performed by an immunoassay technology, a mass spectrometry analysis method, a chromatography method, or a combination of such methods.

\* \* \* \* \*